United States Patent
Masliah et al.

(10) Patent No.: US 8,946,165 B2
(45) Date of Patent: Feb. 3, 2015

(54) COMPOUNDS FOR REVERSING AND INHIBITING PROTEIN AGGREGATION, AND METHODS FOR MAKING AND USING THEM

(75) Inventors: Eliezer Masliah, San Diego, CA (US); Brian Spencer, San Diego, CA (US); Edward Rockenstein, Chula Vista, CA (US); Robert Marr, North Chicago, IL (US)

(73) Assignee: The Regents of the University of California, Oakland, CA (US)

( * ) Notice: Subject to any disclaimer, the term of this patent is extended or adjusted under 35 U.S.C. 154(b) by 447 days.

(21) Appl. No.: 13/119,400

(22) PCT Filed: Sep. 29, 2009

(86) PCT No.: PCT/US2009/058883
§ 371 (c)(1),
(2), (4) Date: Apr. 27, 2011

(87) PCT Pub. No.: WO2010/037135
PCT Pub. Date: Apr. 1, 2010

(65) Prior Publication Data
US 2011/0223240 A1   Sep. 15, 2011

Related U.S. Application Data

(60) Provisional application No. 61/101,058, filed on Sep. 29, 2008.

(51) Int. Cl.
*A61K 38/00* (2006.01)
*C07K 14/47* (2006.01)
*C07K 19/00* (2006.01)

(52) U.S. Cl.
CPC ............. *C07K 14/4711* (2013.01); *C07K 19/00* (2013.01); *A61K 38/00* (2013.01)
USPC ....................................................... 514/17.8

(58) Field of Classification Search
CPC ..... A61K 38/00; C07K 14/4711; C07K 19/00
See application file for complete search history.

(56) References Cited

U.S. PATENT DOCUMENTS

| | | | | |
|---|---|---|---|---|
| 5,442,043 | A * | 8/1995 | Fukuta et al. | 530/303 |
| 6,627,601 | B2 * | 9/2003 | Shashoua | 514/1.3 |
| 7,265,090 | B2 * | 9/2007 | Sung et al. | 514/1.2 |
| 2004/0038302 | A1 | 2/2004 | Nitsch et al. | |
| 2005/0170359 | A1 | 8/2005 | Zlokovic | |
| 2005/0239062 | A1 | 10/2005 | Zlokovic | |
| 2005/0271625 | A1 * | 12/2005 | Nash et al. | 424/93.2 |
| 2006/0198833 | A1 * | 9/2006 | Verma et al. | 424/94.61 |

OTHER PUBLICATIONS

Chang, Bong Ho, International Search Report, PCT/US2009/058883, Korean Intellectual Property Office, May 31, 2010.
Chang, Bong Ho, Written Opinion, PCT/US2009/058883, Korean Intellectual Property Office, May 31, 2010.
Giordan et al., "Systemic and Brain Metabolic Dysfunction As a New Paradigm for Approaching Alzheimer's Dementia", Neurochemical Research, 2007, vol. 32, pp. 555-567.
Ito et al., "Cerebral Clearance of Human Amyloid-beta Peptide (1-40) Across the Blood-brain Barrier is Reduced by Self-aggregation and Formation of Low-density Lipoprotein Receptor-related Protein-1 Ligand Complexes", Journal of Neurochemistry, 2007, vol. 103, pp. 2482-2490.
Jones et al., "Blood-Brain Barrier Transport of Therapeutics via Receptor-Mediation", Pharmaceutical Research, 2007, vol. 24, No. 9, pp. 1759-1771.
Klunk et al., "Imaging Brain Amyloid in Alzheimer's Disease with Pittsburgh Compound-B", Annals of Neurology, 2004, vol. 55, pp. 306-319.
Morelli et al., "The Degradation of Amyloid b As a Therapeutic Strategy in Alzheimer's Disease and Cerebrovascular Amyloidoses", Neurochemical Research, 2002, vol. 27, No. 11, pp. 1387-1399.

* cited by examiner

*Primary Examiner* — Thomas S Heard
(74) *Attorney, Agent, or Firm* — Gregory P. Einhorn; Gavrilovich, Dodd & Lindsey LLP

(57) ABSTRACT

The invention provides compositions for increasing the clearance of protein aggregates, and pharmaceutical compositions comprising them, and methods for making and using them, including methods for accelerating protein aggregate clearance in the CNS, e.g., for treating diseases that are characterized by protein aggregation—including some degenerative neurological diseases such as Parkinson's disease. In one aspect, the compositions of the invention specifically target synuclein, beta-amyloid and/or tau protein aggregates, and the methods of the invention can be used to specifically prevent, reverse, slow or inhibit synuclein, beta-amyloid and/or tau protein aggregation. In alternative embodiments, the compositions and methods of the invention, are used to treat, prevent, reverse (partially or completely) or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent or ameliorate (including slowing the progression of) Parkinson's disease, fronto-temporal dementia (FTD), Alzheimer's Disease (AD), Lewy body disease (LBD) and Multiple system atrophy (MSA).

16 Claims, 9 Drawing Sheets

SEQUENCE LISTING

```
<160> NUMBER OF SEQ ID NOS: 11

<210> SEQ ID NO 1
<211> LENGTH: 764
<212> TYPE: PRT
<213> ORGANISM: artificial sequence
<220> FEATURE:
<223> OTHER INFORMATION: syntthetic polypeptide

<400> SEQUENCE: 1

Met Ser Ala Leu Leu Ile Leu Ala Leu Val Gly Ala Ala Val Ala Asp
1               5                   10                  15

Tyr Lys Asp Asp Asp Asp Lys Thr Gly Ser Ser Val Ile Asp Ala Leu
            20                  25                  30

Gln Tyr Lys Leu Glu Gly Thr Thr Arg Leu Thr Arg Lys Arg Gly Leu
        35                  40                  45

Lys Leu Ala Thr Ala Leu Ser Leu Ser Asn Lys Phe Val Glu Gly Ser
    50                  55                  60

Thr Gly Tyr Asp Asp Gly Ile Cys Lys Ser Ser Asp Cys Ile Lys Ser
65                  70                  75                  80

Ala Ala Arg Leu Ile Gln Asn Met Asp Ala Thr Thr Glu Pro Cys Arg
                85                  90                  95

Asp Phe Phe Lys Tyr Ala Cys Gly Gly Trp Leu Lys Arg Asn Val Ile
            100                 105                 110

Pro Glu Thr Ser Ser Arg Tyr Gly Asn Phe Asp Ile Leu Arg Asp Glu
        115                 120                 125

Leu Glu Val Val Leu Lys Asp Val Leu Gln Pro Lys Thr Glu Asp
    130                 135                 140

Ile Val Ala Val Gln Lys Ala Lys Ala Leu Tyr Arg Ser Cys Ile Asn
145                 150                 155                 160

Glu Ser Ala Ile Asp Ser Arg Gly Gly Glu Pro Leu Leu Lys Leu Leu
                165                 170                 175

Pro Asp Ile Tyr Gly Trp Pro Val Ala Thr Glu Asn Trp Glu Gln Lys
            180                 185                 190
```

Tyr Gly Ala Ser Trp Thr Ala Glu Lys Ala Ile Ala Gln Leu Asn Ser
                195                 200                 205
Lys Tyr Gly Lys Lys Val Leu Ile Asn Leu Phe Val Gly Thr Asp Asp
        210                 215                 220
Lys Asn Ser Val Asn His Val Ile His Ile Asp Gln Pro Arg Leu Gly
225                 230                 235                 240
Leu Pro Ser Arg Asp Tyr Tyr Glu Cys Thr Gly Ile Tyr Lys Glu Ala
                245                 250                 255
Cys Thr Ala Tyr Val Asp Phe Met Ile Ser Val Ala Arg Leu Ile Arg
                260                 265                 270
Gln Glu Glu Arg Leu Pro Ile Asp Glu Asn Gln Leu Ala Leu Glu Met
                275                 280                 285
Asn Lys Val Met Glu Leu Glu Lys Glu Ile Ala Asn Ala Thr Ala Lys
                290                 295                 300
Pro Glu Asp Arg Asn Asp Pro Met Leu Leu Tyr Asn Lys Met Arg Leu
305                 310                 315                 320
Ala Gln Ile Gln Asn Asn Phe Ser Leu Glu Ile Asn Gly Lys Pro Phe
                325                 330                 335
Ser Trp Leu Asn Phe Thr Asn Glu Ile Met Ser Thr Val Asn Ile Ser
                340                 345                 350
Ile Thr Asn Glu Glu Asp Val Val Tyr Ala Pro Glu Tyr Leu Thr
                355                 360                 365
Lys Leu Lys Pro Ile Leu Thr Lys Ser Ala Arg Asp Leu Gln Asn Leu
                370                 375                 380
Met Ser Trp Arg Phe Ile Met Asp Leu Val Ser Ser Leu Ser Arg Thr
385                 390                 395                 400
Tyr Lys Glu Ser Arg Asn Ala Phe Arg Lys Ala Leu Tyr Gly Thr Thr
                405                 410                 415
Ser Glu Thr Ala Thr Trp Arg Arg Cys Ala Asn Tyr Val Asn Gly Asn
                420                 425                 430
Met Glu Asn Ala Val Gly Arg Leu Tyr Val Glu Ala Ala Phe Ala Gly
                435                 440                 445
Glu Ser Lys His Val Val Glu Asp Leu Ile Ala Gln Ile Arg Glu Val
                450                 455                 460
Phe Ile Gln Thr Leu Asp Asp Leu Thr Trp Met Asp Ala Glu Thr Lys
465                 470                 475                 480
Lys Arg Ala Glu Glu Lys Ala Leu Ala Ile Lys Glu Arg Ile Gly Tyr
                485                 490                 495
Pro Asp Asp Ile Val Ser Asn Asp Asn Lys Leu Asn Asn Glu Tyr Leu
                500                 505                 510
Glu Leu Asn Tyr Lys Glu Asp Glu Tyr Phe Glu Asn Ile Ile Gln Asn
                515                 520                 525
Leu Lys Phe Ser Gln Ser Lys Gln Leu Lys Lys Leu Arg Glu Lys Val
                530                 535                 540
Asp Lys Asp Glu Trp Ile Ser Gly Ala Ala Val Val Asn Ala Phe Tyr
545                 550                 555                 560
Ser Ser Gly Arg Asn Gln Ile Val Phe Pro Ala Gly Ile Leu Gln Pro
                565                 570                 575
Pro Phe Phe Ser Ala Gln Gln Ser Asn Ser Leu Asn Tyr Gly Gly Ile
                580                 585                 590
Gly Met Val Ile Gly His Glu Ile Thr His Gly Phe Asp Asp Asn Gly
                595                 600                 605
Arg Asn Phe Asn Lys Asp Gly Asp Leu Val Asp Trp Trp Thr Gln Gln

```
                610             615             620
Ser Ala Ser Asn Phe Lys Glu Gln Ser Gln Cys Met Val Tyr Gln Tyr
625             630             635             640

Gly Asn Phe Ser Trp Asp Leu Ala Gly Gly Gln His Leu Asn Gly Ile
            645             650             655

Asn Thr Leu Gly Glu Asn Ile Ala Asp Asn Gly Gly Leu Gly Gln Ala
            660             665             670

Tyr Arg Ala Tyr Gln Asn Tyr Ile Lys Lys Asn Gly Glu Glu Lys Leu
            675             680             685

Leu Pro Gly Leu Asp Leu Asn His Lys Gln Leu Phe Phe Leu Asn Phe
            690             695             700

Ala Gln Val Trp Cys Gly Thr Tyr Arg Pro Glu Tyr Ala Val Asn Ser
705             710             715             720

Ile Lys Thr Asp Val His Ser Pro Gly Asn Phe Arg Ile Ile Gly Thr
                725             730             735

Leu Gln Asn Ser Ala Glu Phe Ser Glu Ala Phe His Cys Arg Lys Asn
                740             745             750

Ser Tyr Met Asn Pro Glu Lys Lys Cys Arg Val Trp
            755             760

<210> SEQ ID NO 2
<211> LENGTH: 750
<212> TYPE: PRT
<213> ORGANISM: Homo sapiens

<400> SEQUENCE: 2

Met Gly Lys Ser Glu Ser Gln Met Asp Ile Thr Asp Ile Asn Thr Pro
1               5               10              15

Lys Pro Lys Lys Lys Gln Arg Trp Thr Pro Leu Glu Ile Ser Leu Ser
            20              25              30

Val Leu Val Leu Leu Leu Thr Ile Ile Ala Val Thr Met Ile Ala Leu
            35              40              45

Tyr Ala Thr Tyr Asp Asp Gly Ile Cys Lys Ser Ser Asp Cys Ile Lys
        50              55              60

Ser Ala Ala Arg Leu Ile Gln Asn Met Asp Ala Thr Thr Glu Pro Cys
65              70              75              80

Thr Asp Phe Phe Lys Tyr Ala Cys Gly Gly Trp Leu Lys Arg Asn Val
            85              90              95

Ile Pro Glu Thr Ser Ser Arg Tyr Gly Asn Phe Asp Ile Leu Arg Asp
            100             105             110

Glu Leu Glu Val Val Leu Lys Asp Val Leu Gln Glu Pro Lys Thr Glu
            115             120             125

Asp Ile Val Ala Val Gln Lys Ala Lys Ala Leu Tyr Arg Ser Cys Ile
        130             135             140

Asn Glu Ser Ala Ile Asp Ser Arg Gly Gly Glu Pro Leu Leu Lys Leu
145             150             155             160

Leu Pro Asp Ile Tyr Gly Trp Pro Val Ala Thr Glu Asn Trp Glu Gln
            165             170             175

Lys Tyr Gly Ala Ser Trp Thr Ala Glu Lys Ala Ile Ala Gln Leu Asn
            180             185             190

Ser Lys Tyr Gly Lys Lys Val Leu Ile Asn Leu Phe Val Gly Thr Asp
        195             200             205

Asp Lys Asn Ser Val Asn His Val Ile His Ile Asp Gln Pro Arg Leu
    210             215             220
```

-continued

```
Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
            245                 250                 255

Arg Gln Glu Glu Arg Leu Pro Ile Asp Glu Asn Gln Leu Ala Leu Glu
        260                 265                 270

Met Asn Lys Val Met Glu Leu Glu Lys Glu Ile Ala Asn Ala Thr Ala
    275                 280                 285

Lys Pro Glu Asp Arg Asn Asp Pro Met Leu Leu Tyr Asn Lys Met Thr
290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
            325                 330                 335

Ser Ile Thr Asn Glu Glu Asp Val Val Val Tyr Ala Pro Glu Tyr Leu
        340                 345                 350

Thr Lys Leu Lys Pro Ile Leu Thr Lys Tyr Ser Ala Arg Asp Leu Gln
    355                 360                 365

Asn Leu Met Ser Trp Arg Phe Ile Met Asp Leu Val Ser Ser Leu Ser
370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
            405                 410                 415

Gly Asn Met Glu Asn Ala Val Gly Arg Leu Tyr Val Glu Ala Ala Phe
        420                 425                 430

Ala Gly Glu Ser Lys His Val Val Glu Asp Leu Ile Ala Gln Ile Arg
    435                 440                 445

Glu Val Phe Ile Gln Thr Leu Asp Asp Leu Thr Trp Met Asp Ala Glu
450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
            485                 490                 495

Tyr Leu Glu Leu Asn Tyr Lys Glu Asp Glu Tyr Phe Glu Asn Ile Ile
        500                 505                 510

Gln Asn Leu Lys Phe Ser Gln Ser Lys Gln Leu Lys Lys Leu Arg Glu
    515                 520                 525

Lys Val Asp Lys Asp Glu Trp Ile Ser Gly Ala Ala Val Val Asn Ala
530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
            565                 570                 575

Gly Ile Gly Met Val Ile Gly His Glu Ile Thr His Gly Phe Asp Asp
        580                 585                 590

Asn Gly Arg Asn Phe Asn Lys Asp Gly Asp Leu Val Asp Trp Trp Thr
    595                 600                 605

Gln Gln Ser Ala Ser Asn Phe Lys Glu Gln Ser Gln Cys Met Val Tyr
610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
```

```
                     645                 650                 655
Gln Ala Tyr Arg Ala Tyr Gln Asn Tyr Ile Lys Lys Asn Gly Glu Glu
                660                 665                 670

Lys Leu Leu Pro Gly Leu Asp Leu Asn His Lys Gln Leu Phe Phe Leu
            675                 680                 685

Asn Phe Ala Gln Val Trp Cys Gly Thr Tyr Arg Pro Glu Tyr Ala Val
        690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750

<210> SEQ ID NO 3
<211> LENGTH: 450
<212> TYPE: PRT
<213> ORGANISM: Homo sapiens

<400> SEQUENCE: 3

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
        35                  40                  45

Thr Ala Gln Ala Lys Pro Gly Glu Thr Gln Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Arg Leu Asp Gln
    210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270
```

```
Thr Phe His Ile Trp His Ser Gly Gln Phe Gly Thr Ile Asn Asn Phe
            275                 280                 285

Arg Leu Gly Arg Leu Pro Ser Val Pro Val Glu Trp Asn Glu Ile Asn
290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
                325                 330                 335

Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
        355                 360                 365

Met Val Ala Phe Leu Asp Cys Val Gln Gln Phe Lys Glu Glu Val Glu
    370                 375                 380

Lys Gly Glu Thr Arg Phe Cys Leu Pro Tyr Arg Met Asp Val Glu Lys
385                 390                 395                 400

Gly Lys Ile Glu Asp Thr Gly Gly Ser Gly Ser Tyr Ser Ile Lys
                405                 410                 415

Thr Gln Phe Asn Ser Glu Glu Gln Trp Thr Lys Ala Leu Lys Phe Met
            420                 425                 430

Leu Thr Asn Leu Lys Trp Gly Leu Ala Trp Val Ser Ser Gln Phe Tyr
        435                 440                 445

Asn Lys
    450

<210> SEQ ID NO 4
<211> LENGTH: 1019
<212> TYPE: PRT
<213> ORGANISM: Homo sapiens

<400> SEQUENCE: 4

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190
```

```
Asn Val Met Asn Asp Ala Trp Arg Leu Phe Gln Leu Glu Lys Ala Thr
        195                 200                 205
Gly Asn Pro Lys His Pro Phe Ser Lys Phe Gly Thr Gly Asn Lys Tyr
    210                 215                 220
Thr Leu Glu Thr Arg Pro Asn Gln Glu Gly Ile Asp Val Arg Gln Glu
225                 230                 235                 240
Leu Leu Lys Phe His Ser Ala Tyr Tyr Ser Ser Asn Leu Met Ala Val
                245                 250                 255
Cys Val Leu Gly Arg Glu Ser Leu Asp Asp Leu Thr Asn Leu Val Val
                260                 265                 270
Lys Leu Phe Ser Glu Val Glu Asn Lys Asn Val Pro Leu Pro Glu Phe
            275                 280                 285
Pro Glu His Pro Phe Gln Glu Glu His Leu Lys Gln Leu Tyr Lys Ile
        290                 295                 300
Val Pro Ile Lys Asp Ile Arg Asn Leu Tyr Val Thr Phe Pro Ile Pro
305                 310                 315                 320
Asp Leu Gln Lys Tyr Tyr Lys Ser Asn Pro Gly His Tyr Leu Gly His
                325                 330                 335
Leu Ile Gly His Glu Gly Pro Gly Ser Leu Leu Ser Gly Leu Lys Ser
                340                 345                 350
Lys Gly Trp Val Asn Thr Leu Val Gly Gly Gln Lys Glu Gly Ala Arg
            355                 360                 365
Gly Phe Met Phe Phe Ile Ile Asn Val Asp Leu Thr Glu Glu Gly Leu
        370                 375                 380
Leu His Val Glu Asp Ile Ile Leu His Met Phe Gln Tyr Ile Gln Lys
385                 390                 395                 400
Leu Arg Ala Glu Gly Pro Gln Glu Trp Val Phe Gln Glu Cys Lys Asp
                405                 410                 415
Leu Asn Ala Val Ala Phe Arg Phe Lys Asp Lys Glu Arg Pro Arg Gly
                420                 425                 430
Tyr Thr Ser Lys Ile Ala Gly Ile Leu His Tyr Tyr Pro Leu Glu Glu
            435                 440                 445
Val Leu Thr Ala Glu Tyr Leu Leu Glu Glu Phe Arg Pro Asp Leu Ile
        450                 455                 460
Glu Met Val Leu Asp Lys Leu Arg Pro Glu Asn Val Arg Val Ala Ile
465                 470                 475                 480
Val Ser Lys Ser Phe Glu Gly Lys Thr Asp Arg Thr Glu Glu Trp Tyr
                485                 490                 495
Gly Thr Gln Tyr Lys Gln Glu Ala Ile Pro Asp Glu Val Ile Lys Lys
            500                 505                 510
Trp Gln Asn Ala Asp Leu Asn Gly Lys Phe Lys Leu Pro Thr Lys Asn
        515                 520                 525
Glu Phe Ile Pro Thr Asn Phe Glu Ile Leu Pro Leu Glu Lys Glu Ala
    530                 535                 540
Thr Pro Tyr Pro Ala Leu Ile Lys Asp Thr Ala Met Ser Lys Leu Trp
545                 550                 555                 560
Phe Lys Gln Asp Asp Lys Phe Phe Leu Pro Lys Ala Cys Leu Asn Phe
                565                 570                 575
Glu Phe Phe Ser Pro Phe Ala Tyr Val Asp Pro Leu His Cys Asn Met
                580                 585                 590
Ala Tyr Leu Tyr Leu Glu Leu Leu Lys Asp Ser Leu Asn Glu Tyr Ala
            595                 600                 605
```

-continued

Tyr Ala Ala Glu Leu Ala Gly Leu Ser Tyr Asp Leu Gln Asn Thr Ile
    610             615             620

Tyr Gly Met Tyr Leu Ser Val Lys Gly Tyr Asn Asp Lys Gln Pro Ile
625             630             635             640

Leu Leu Lys Lys Ile Ile Glu Lys Met Ala Thr Phe Glu Ile Asp Glu
            645             650             655

Lys Arg Phe Glu Ile Ile Lys Glu Ala Tyr Met Arg Ser Leu Asn Asn
            660             665             670

Phe Arg Ala Glu Gln Pro His Gln His Ala Met Tyr Tyr Leu Arg Leu
        675             680             685

Leu Met Thr Glu Val Ala Trp Thr Lys Asp Glu Leu Lys Glu Ala Leu
    690             695             700

Asp Asp Val Thr Leu Pro Arg Leu Lys Ala Phe Ile Pro Gln Leu Leu
705             710             715             720

Ser Arg Leu His Ile Glu Ala Leu Leu His Gly Asn Ile Thr Lys Gln
            725             730             735

Ala Ala Leu Gly Ile Met Gln Met Val Glu Asp Thr Leu Ile Glu His
            740             745             750

Ala His Thr Lys Pro Leu Leu Pro Ser Gln Leu Val Arg Tyr Arg Glu
        755             760             765

Val Gln Leu Pro Asp Arg Gly Trp Phe Val Tyr Gln Gln Arg Asn Glu
    770             775             780

Val His Asn Asn Cys Gly Ile Glu Ile Tyr Tyr Gln Thr Asp Met Gln
785             790             795             800

Ser Thr Ser Glu Asn Met Phe Leu Glu Leu Phe Cys Gln Ile Ile Ser
            805             810             815

Glu Pro Cys Phe Asn Thr Leu Arg Thr Lys Glu Gln Leu Gly Tyr Ile
        820             825             830

Val Phe Ser Gly Pro Arg Arg Ala Asn Gly Ile Gln Gly Leu Arg Phe
    835             840             845

Ile Ile Gln Ser Glu Lys Pro Pro His Tyr Leu Glu Ser Arg Val Glu
    850             855             860

Ala Phe Leu Ile Thr Met Glu Lys Ser Ile Glu Asp Met Thr Glu Glu
865             870             875             880

Ala Phe Gln Lys His Ile Gln Ala Leu Ala Ile Arg Arg Leu Asp Lys
            885             890             895

Pro Lys Lys Leu Ser Ala Glu Cys Ala Lys Tyr Trp Gly Glu Ile Ile
            900             905             910

Ser Gln Gln Tyr Asn Phe Asp Arg Asp Asn Thr Glu Val Ala Tyr Leu
        915             920             925

Lys Thr Leu Thr Lys Glu Asp Ile Ile Lys Phe Tyr Lys Glu Met Leu
    930             935             940

Ala Val Asp Ala Pro Arg Arg His Lys Val Ser Val His Val Leu Ala
945             950             955             960

Arg Glu Met Asp Ser Cys Pro Val Val Gly Glu Phe Pro Cys Gln Asn
            965             970             975

Asp Ile Asn Leu Ser Gln Ala Pro Ala Leu Pro Gln Pro Glu Val Ile
            980             985             990

Gln Asn Met Thr Glu Phe Lys Arg Gly Leu Pro Leu Phe Pro Leu Val
        995             1000            1005

Lys Pro His Ile Asn Phe Met Ala Ala Lys Leu
    1010            1015

```
<210> SEQ ID NO 5
<211> LENGTH: 398
<212> TYPE: PRT
<213> ORGANISM: Homo sapiens

<400> SEQUENCE: 5

Met Glu Ser Val Leu Ser Lys Tyr Glu Asp Gln Ile Thr Ile Phe Thr
1               5                   10                  15

Asp Tyr Leu Glu Glu Tyr Pro Asp Thr Asp Glu Leu Val Trp Ile Leu
            20                  25                  30

Gly Lys Gln His Leu Leu Lys Thr Glu Lys Ser Lys Leu Leu Ser Asp
        35                  40                  45

Ile Ser Ala Arg Leu Trp Phe Thr Tyr Arg Arg Lys Phe Ser Pro Ile
50                  55                  60

Gly Gly Thr Gly Pro Ser Ser Asp Ala Gly Trp Gly Cys Met Leu Arg
65                  70                  75                  80

Cys Gly Gln Met Met Leu Ala Gln Ala Leu Ile Cys Arg His Leu Gly
                85                  90                  95

Arg Asp Trp Ser Trp Glu Lys Gln Lys Glu Gln Pro Lys Glu Tyr Gln
            100                 105                 110

Arg Ile Leu Gln Cys Phe Leu Asp Arg Lys Asp Cys Cys Tyr Ser Ile
        115                 120                 125

His Gln Met Ala Gln Met Gly Val Gly Glu Gly Lys Ser Ile Gly Glu
130                 135                 140

Trp Phe Gly Pro Asn Thr Val Ala Gln Val Leu Lys Lys Leu Ala Leu
145                 150                 155                 160

Phe Asp Glu Trp Asn Ser Leu Ala Val Tyr Val Ser Met Asp Asn Thr
                165                 170                 175

Val Val Ile Glu Asp Ile Lys Lys Met Cys Arg Val Leu Pro Leu Ser
            180                 185                 190

Ala Asp Thr Ala Gly Asp Arg Pro Pro Asp Ser Leu Thr Ala Ser Asn
        195                 200                 205

Gln Ser Lys Gly Thr Ser Ala Tyr Cys Ser Ala Trp Lys Pro Leu Leu
210                 215                 220

Leu Ile Val Pro Leu Arg Leu Gly Ile Asn Gln Ile Asn Pro Val Tyr
225                 230                 235                 240

Val Asp Ala Phe Lys Glu Cys Phe Lys Met Pro Gln Ser Leu Gly Ala
                245                 250                 255

Leu Gly Gly Lys Pro Asn Asn Ala Tyr Tyr Phe Ile Gly Phe Leu Gly
            260                 265                 270

Asp Glu Leu Ile Phe Leu Asp Pro His Thr Thr Gln Thr Phe Val Asp
        275                 280                 285

Thr Glu Glu Asn Gly Thr Val Asn Asp Gln Thr Phe His Cys Leu Gln
290                 295                 300

Ser Pro Gln Arg Met Asn Ile Leu Asn Leu Asp Pro Ser Val Ala Leu
305                 310                 315                 320

Gly Phe Phe Cys Lys Glu Glu Lys Asp Phe Asp Asn Trp Cys Ser Leu
                325                 330                 335

Val Gln Lys Glu Ile Leu Lys Glu Asn Leu Arg Met Phe Glu Leu Val
            340                 345                 350

Gln Lys His Pro Ser His Trp Pro Pro Phe Val Pro Pro Ala Lys Pro
        355                 360                 365

Glu Val Thr Thr Thr Gly Ala Glu Phe Ile Asp Ser Thr Glu Gln Leu
370                 375                 380
```

```
Glu Glu Phe Asp Leu Glu Asp Phe Glu Ile Leu Ser Val
385                 390                 395
```

<210> SEQ ID NO 6
<211> LENGTH: 336
<212> TYPE: PRT
<213> ORGANISM: Homo sapiens

<400> SEQUENCE: 6

```
Met Glu Ser Val Leu Ser Lys Tyr Glu Asp Gln Ile Thr Ile Phe Thr
1               5                   10                  15

Asp Tyr Leu Glu Glu Tyr Pro Asp Thr Asp Glu Leu Val Trp Ile Leu
            20                  25                  30

Gly Lys Gln His Leu Leu Lys Thr Glu Lys Ser Lys Leu Leu Ser Asp
        35                  40                  45

Ile Ser Ala Arg Leu Trp Phe Thr Tyr Arg Arg Lys Phe Ser Pro Ile
    50                  55                  60

Gly Gly Thr Gly Pro Ser Ser Asp Ala Gly Trp Gly Cys Met Leu Arg
65                  70                  75                  80

Cys Gly Gln Met Met Leu Ala Gln Ala Leu Ile Cys Arg His Leu Gly
                85                  90                  95

Arg Asp Trp Ser Trp Glu Lys Gln Lys Glu Gln Pro Lys Glu Tyr Gln
            100                 105                 110

Arg Ile Leu Gln Cys Phe Leu Asp Arg Lys Asp Cys Cys Tyr Ser Ile
        115                 120                 125

His Gln Met Ala Gln Met Gly Val Gly Glu Gly Lys Ser Ile Gly Glu
    130                 135                 140

Trp Phe Gly Pro Asn Thr Val Ala Gln Val Leu Lys Lys Leu Ala Leu
145                 150                 155                 160

Phe Asp Glu Trp Asn Ser Leu Ala Val Tyr Val Ser Met Asp Asn Thr
                165                 170                 175

Val Val Ile Glu Asp Ile Lys Lys Met Cys Arg Val Leu Pro Leu Ser
            180                 185                 190

Ala Asp Thr Ala Gly Asp Arg Pro Pro Asp Ser Leu Thr Ala Ser Asn
        195                 200                 205

Gln Ser Asp Glu Leu Ile Phe Leu Asp Pro His Thr Thr Gln Thr Phe
    210                 215                 220

Val Asp Thr Glu Glu Asn Gly Thr Val Asn Asp Gln Thr Phe His Cys
225                 230                 235                 240

Leu Gln Ser Pro Gln Arg Met Asn Ile Leu Asn Leu Asp Pro Ser Val
                245                 250                 255

Ala Leu Gly Phe Phe Cys Lys Glu Glu Lys Asp Phe Asp Asn Trp Cys
            260                 265                 270

Ser Leu Val Gln Lys Glu Ile Leu Lys Glu Asn Leu Arg Met Phe Glu
        275                 280                 285

Leu Val Gln Lys His Pro Ser His Trp Pro Pro Phe Val Pro Pro Ala
    290                 295                 300

Lys Pro Glu Val Thr Thr Thr Gly Ala Glu Phe Ile Asp Ser Thr Glu
305                 310                 315                 320

Gln Leu Glu Glu Phe Asp Leu Glu Asp Phe Glu Ile Leu Ser Val
                325                 330                 335
```

<210> SEQ ID NO 7
<211> LENGTH: 458
<212> TYPE: PRT
<213> ORGANISM: Homo sapiens

<400> SEQUENCE: 7

Met Glu Ala Thr Gly Thr Asp Glu Val Asp Lys Leu Lys Thr Lys Phe
1               5                   10                  15

Ile Ser Ala Trp Asn Asn Met Lys Tyr Ser Trp Val Leu Lys Thr Lys
            20                  25                  30

Thr Tyr Phe Ser Arg Asn Ser Pro Val Leu Leu Gly Lys Cys Tyr
        35                  40                  45

His Phe Lys Tyr Glu Asp Glu Asp Lys Thr Leu Pro Ala Glu Ser Gly
    50                  55                  60

Cys Thr Ile Glu Asp His Val Ile Ala Gly Asn Val Glu Glu Phe Arg
65                  70                  75                  80

Lys Asp Phe Ile Ser Arg Ile Trp Leu Thr Tyr Arg Glu Glu Phe Pro
                85                  90                  95

Gln Ile Glu Gly Ser Ala Leu Thr Thr Asp Cys Gly Trp Gly Cys Thr
            100                 105                 110

Leu Arg Thr Gly Gln Met Leu Leu Ala Gln Gly Leu Ile Leu His Phe
        115                 120                 125

Leu Gly Arg Ala Trp Thr Trp Pro Asp Ala Leu Asn Ile Glu Asn Ser
130                 135                 140

Asp Ser Glu Ser Trp Thr Ser His Thr Val Lys Lys Phe Thr Ala Ser
145                 150                 155                 160

Phe Glu Ala Ser Leu Ser Gly Glu Arg Glu Phe Lys Thr Pro Thr Ile
                165                 170                 175

Ser Leu Lys Glu Thr Ile Gly Lys Tyr Ser Asp Asp His Glu Met Arg
            180                 185                 190

Asn Glu Val Tyr His Arg Lys Ile Ile Ser Trp Phe Gly Asp Ser Pro
        195                 200                 205

Leu Ala Leu Phe Gly Leu His Gln Leu Ile Glu Tyr Gly Lys Lys Ser
210                 215                 220

Gly Lys Lys Ala Gly Asp Trp Tyr Gly Pro Ala Val Val Ala His Ile
225                 230                 235                 240

Leu Arg Lys Ala Val Glu Glu Ala Arg His Pro Asp Leu Gln Gly Ile
                245                 250                 255

Thr Ile Tyr Val Ala Gln Asp Cys Thr Val Tyr Asn Ser Asp Val Ile
            260                 265                 270

Asp Lys Gln Ser Ala Ser Met Thr Ser Asp Asn Ala Asp Asp Lys Ala
        275                 280                 285

Val Ile Ile Leu Val Pro Val Arg Leu Gly Gly Glu Arg Thr Asn Thr
290                 295                 300

Asp Tyr Leu Glu Phe Val Lys Gly Ile Leu Ser Leu Glu Tyr Cys Val
305                 310                 315                 320

Gly Ile Ile Gly Gly Lys Pro Lys Gln Ser Tyr Tyr Phe Ala Gly Phe
                325                 330                 335

Gln Asp Asp Ser Leu Ile Tyr Met Asp Pro His Tyr Cys Gln Ser Phe
            340                 345                 350

Val Asp Val Ser Ile Lys Asp Phe Pro Leu Glu Thr Phe His Cys Pro
        355                 360                 365

Ser Pro Lys Lys Met Ser Phe Arg Lys Met Asp Pro Ser Cys Thr Ile
370                 375                 380

Gly Phe Tyr Cys Arg Asn Val Gln Asp Phe Lys Arg Ala Ser Glu Glu
385                 390                 395                 400

Ile Thr Lys Met Leu Lys Phe Ser Ser Lys Glu Lys Tyr Pro Leu Phe

```
            405                 410                 415
Thr Phe Val Asn Gly His Ser Arg Asp Tyr Asp Phe Thr Ser Thr Thr
            420                 425                 430

Thr Asn Glu Glu Asp Leu Phe Ser Glu Asp Glu Lys Lys Gln Leu Lys
        435                 440                 445

Arg Phe Ser Thr Glu Glu Phe Val Leu Leu
    450                 455

<210> SEQ ID NO 8
<211> LENGTH: 474
<212> TYPE: PRT
<213> ORGANISM: Homo sapiens

<400> SEQUENCE: 8

Met Asn Ser Val Ser Pro Ala Ala Gln Tyr Arg Ser Ser Pro
1               5                   10                  15

Glu Asp Ala Arg Arg Pro Glu Ala Arg Pro Arg Gly Pro Arg
            20                  25                  30

Gly Pro Asp Pro Asn Gly Leu Gly Pro Ser Gly Ala Ser Gly Pro Ala
        35                  40                  45

Leu Gly Ser Pro Gly Ala Gly Pro Ser Glu Pro Asp Glu Val Asp Lys
    50                  55                  60

Phe Lys Ala Lys Phe Leu Thr Ala Trp Asn Asn Val Lys Tyr Gly Trp
65                  70                  75                  80

Val Val Lys Ser Arg Thr Ser Phe Ser Lys Ile Ser Ser Ile His Leu
                85                  90                  95

Cys Gly Arg Arg Tyr Arg Phe Glu Gly Glu Gly Asp Ile Gln Arg Phe
            100                 105                 110

Gln Arg Asp Phe Val Ser Arg Leu Trp Leu Thr Tyr Arg Arg Asp Phe
        115                 120                 125

Pro Pro Leu Pro Gly Gly Cys Leu Thr Ser Asp Cys Gly Trp Gly Cys
    130                 135                 140

Met Leu Arg Ser Gly Gln Met Met Leu Ala Gln Gly Leu Leu Leu His
145                 150                 155                 160

Phe Leu Pro Arg Asp Trp Thr Trp Ala Glu Gly Met Gly Leu Gly Pro
                165                 170                 175

Pro Glu Leu Ser Gly Ser Ala Ser Pro Ser Arg Tyr His Gly Pro Ala
            180                 185                 190

Arg Trp Met Pro Pro Arg Trp Ala Gln Gly Ala Pro Glu Leu Glu Gln
        195                 200                 205

Glu Arg Arg His Arg Gln Ile Val Ser Trp Phe Ala Asp His Pro Arg
    210                 215                 220

Ala Pro Phe Gly Leu His Arg Leu Val Glu Leu Gly Gln Ser Ser Gly
225                 230                 235                 240

Lys Lys Ala Gly Asp Trp Tyr Gly Pro Ser Leu Val Ala His Ile Leu
                245                 250                 255

Arg Lys Ala Val Glu Ser Cys Ser Asp Val Thr Arg Leu Val Val Tyr
            260                 265                 270

Val Ser Gln Asp Cys Thr Val Tyr Lys Ala Asp Val Ala Arg Leu Val
        275                 280                 285

Ala Arg Pro Asp Pro Thr Ala Glu Trp Lys Ser Val Val Ile Leu Val
    290                 295                 300

Pro Val Arg Leu Gly Gly Glu Thr Leu Asn Pro Val Tyr Val Pro Cys
305                 310                 315                 320
```

```
Val Lys Glu Leu Leu Arg Cys Glu Leu Cys Leu Gly Ile Met Gly Gly
            325                 330                 335

Lys Pro Arg His Ser Leu Tyr Phe Ile Gly Tyr Gln Asp Asp Phe Leu
        340                 345                 350

Leu Tyr Leu Asp Pro His Tyr Cys Gln Pro Thr Val Asp Val Ser Gln
            355                 360                 365

Ala Asp Phe Pro Leu Glu Ser Phe His Cys Thr Ser Pro Arg Lys Met
370                 375                 380

Ala Phe Ala Lys Met Asp Pro Ser Cys Thr Val Gly Phe Tyr Ala Gly
385                 390                 395                 400

Asp Arg Lys Glu Phe Glu Thr Leu Cys Ser Glu Leu Thr Arg Val Leu
                405                 410                 415

Ser Ser Ser Ser Ala Thr Glu Arg Tyr Pro Met Phe Thr Leu Ala Glu
            420                 425                 430

Gly His Ala Gln Asp His Ser Leu Asp Asp Leu Cys Ser Gln Leu Ala
            435                 440                 445

Gln Pro Thr Leu Arg Leu Pro Arg Thr Gly Arg Leu Arg Ala Lys
        450                 455                 460

Arg Pro Ser Ser Glu Asp Phe Val Phe Leu
465                 470

<210> SEQ ID NO 9
<211> LENGTH: 156
<212> TYPE: PRT
<213> ORGANISM: Homo sapiens

<400> SEQUENCE: 9

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
        115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155

<210> SEQ ID NO 10
<211> LENGTH: 147
<212> TYPE: PRT
<213> ORGANISM: Homo sapiens

<400> SEQUENCE: 10

Met Ala Ser His Arg Leu Leu Leu Leu Cys Leu Ala Gly Leu Val Phe
1               5                   10                  15
```

```
Val Ser Glu Ala Gly Pro Thr Gly Thr Gly Ser Lys Cys Pro Leu
         20                  25                  30

Met Val Lys Val Leu Asp Ala Val Arg Gly Ser Pro Ala Ile Asn Val
         35                  40                  45

Ala Val His Val Phe Arg Lys Ala Ala Asp Asp Thr Trp Glu Pro Phe
         50                  55                  60

Ala Ser Gly Lys Thr Ser Glu Ser Gly Glu Leu His Gly Leu Thr Thr
65                   70                  75                  80

Glu Glu Glu Phe Val Glu Gly Ile Tyr Lys Val Glu Ile Asp Thr Lys
                 85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Thr Asn
130                 135                 140

Pro Lys Glu
145

<210> SEQ ID NO 11
<211> LENGTH: 211
<212> TYPE: PRT
<213> ORGANISM: Homo sapiens

<400> SEQUENCE: 11

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
50                  55                  60

Asp Arg Leu Arg Pro Leu Ser Tyr Pro Gln Thr Val Gly Glu Thr Tyr
65                  70                  75                  80

Gly Lys Asp Ile Thr Ser Arg Gly Lys Asp Lys Pro Ile Ala Asp Val
                85                  90                  95

Phe Leu Ile Cys Phe Ser Leu Val Ser Pro Ala Ser Phe Glu Asn Val
            100                 105                 110

Arg Ala Lys Trp Tyr Pro Glu Val Arg His His Cys Pro Asn Thr Pro
            115                 120                 125

Ile Ile Leu Val Gly Thr Lys Leu Asp Leu Arg Asp Asp Lys Asp Thr
130                 135                 140

Ile Glu Lys Leu Lys Glu Lys Lys Leu Thr Pro Ile Thr Tyr Pro Gln
145                 150                 155                 160

Gly Leu Ala Met Ala Lys Glu Ile Gly Ala Val Lys Tyr Leu Glu Cys
                165                 170                 175

Ser Ala Leu Thr Gln Arg Gly Leu Lys Thr Val Phe Asp Glu Ala Ile
            180                 185                 190

Arg Ala Val Leu Cys Pro Pro Val Lys Lys Arg Lys Arg Lys Cys
            195                 200                 205

Leu Leu Leu
    210
```

COMPOUNDS FOR REVERSING AND INHIBITING PROTEIN AGGREGATION, AND METHODS FOR MAKING AND USING THEM

STATEMENT AS TO FEDERALLY SPONSORED RESEARCH

This invention was made with government support under grant numbers AG018440, SUBR2094-A (AG022074), SUBR2094-B (AG022074), awarded by the National Institute of General Medical, National Institutes of Health (NIH), DHHS. The government has certain rights in the invention.

CROSS-REFERENCE TO RELATED APPLICATIONS

This United States utility patent application is the §371 national phase of PCT international patent application no. PCT/US09/58883, having an international filing date of Sep. 29, 2009, which claims benefit of priority to U.S. Provisional Patent Application Ser. No. 61/101,058, filed Sep. 29, 2008. The aforementioned applications are expressly incorporated herein by reference in their entirety and for all purposes.

TECHNICAL FIELD

This invention generally relates to protein chemistry, cell biology, neuroscience and medicine. The invention provides compositions for increasing the clearance of protein aggregates such as amyloid beta protein (Aβ) aggregates, and pharmaceutical compositions comprising them, and methods for making and using them, including methods for accelerating protein aggregate clearance in the CNS, e.g., for treating diseases that are characterized by (e.g., caused or aggravated by) protein aggregation—including a degenerative neurological disease such as Parkinson's disease, Alzheimer's Disease (AD), fronto-temporal dementia (FTD), Lewy body disease (LBD), a hereditary systemic amyloidosis and Multiple system atrophy (MSA). In one aspect, the compositions of the invention specifically target synuclein, beta-amyloid and/or tau protein aggregates, and the methods of the invention can be used to specifically prevent, reverse, slow or inhibit synuclein, beta-amyloid and/or tau protein aggregation.

In alternative embodiments, the compositions and methods of the invention, including the synuclein, beta-amyloid and/or tau protein aggregation inhibiting compositions of the invention, and the pharmaceutical compositions comprising them, are used to treat, prevent, reverse (partially or completely) or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent, reverse and/or ameliorate (including slowing the progression of) Parkinson's disease, Alzheimer's Disease (AD), fronto-temporal dementia (FTD), Lewy body disease (LBD) and Multiple system atrophy (MSA).

BACKGROUND

Abnormal accumulation of amyloid beta protein (Aβ) and/or tau in the nervous system results in progressive damage to neurons leading to Alzheimer's Disease (AD) and fronto-temporal dementia (FTD). These devastating disorders affect over 5 million people in the US alone. Aβ is a 40 to 42 amino acid long peptide derived from the proteolysis of amyloid precursor protein (APP) by the gamma and beta-secretases. Accumulation of oligomeric forms of Aβ promotes degeneration by damaging the synaptic connections among neurons. In AD, accumulation of Aβ oligomers may be the result of alterations in the balance between the rate of Aβ synthesis, aggregation and clearance. Although most recent therapies for AD have been focused at blocking synthesis or aggregation of Aβ, relatively less has been done to promote clearance. The clearance of Aβ depends on removal by: i) chaperones (e.g., apoE, beta-2M, HSP's), ii) degrading enzymes (e.g., neprilysin (NEP), insulin-degrading enzyme (IDE), EDE), iii) non-lysosomal degradation (e.g., proteosome) and/or lysosomal degradation (e.g., by autophagy).

The use of polypeptides that can increase the clearance of Aβ aggregates via degradation (e.g., NEP, IDE), autophagy (e.g., Beclin), lysosomal enzymes (e.g., cathepsin) or binding molecules (e.g., apolipoprotein E (apoE), antibodies, beta-2M) has been described. The main problem in all of these cases is that the polypeptides of interest cannot enter into the CNS, or when they do they can only enter at very low levels—below their therapeutic value.

SUMMARY

The invention provides compositions and methods for increasing the clearance of protein aggregates, such as synuclein, tau and/or beta-amyloid (e.g., Aβ) protein aggregates, by delivering to an individual in need thereof specific hybrid or chimeric polypeptides that selectively traffic into the central nervous system (CNS) and target protein aggregations, e.g., tau and/or Aβ, for degradation.

The hybrid or chimeric polypeptides of this invention can be synthesized by recombinant technologies in vitro or in vivo or can be synthetic; e.g., hybrid or chimeric polypeptides of this invention can be delivered orally or enterally, e.g., intravascularly or directly into the CNS, or by in vivo synthesis, e.g., by gene therapy.

In one embodiment, a vector, e.g., a viral vector, drives the production of a fusion polypeptide of this invention in a peripheral organ or organs, e.g., liver and/or spleen. The unique feature of this embodiment is that it allows the trafficking of the specific hybrid or chimeric polypeptides of this invention into the CNS; which in one embodiment is mediated by a fusion with a fragment of the apoB protein, including apoB-secNEP, apoB-Beclin and/or apoB-apoE. Example 1 shows data from inventors' work on the treatment of AD with the exemplary hybrid or chimeric polypeptide of the invention, apoB-secNEP.

The invention provide a novel therapy for AD and related neurodegenerative disorders by increasing the clearance of cytotoxic (e.g., neurotoxic) protein aggregates (e.g., synuclein, tau and/or beta-amyloid (e.g., Aβ) aggregates) via exogenous delivery of hybrid or chimeric polypeptides of the invention having the ability of crossing the blood brain barrier (BBB).

The invention provides compositions for increasing the clearance of protein aggregates, and pharmaceutical compositions comprising them, and methods for making and using them, including methods for initiating and/or accelerating protein aggregate clearance in the CNS, e.g., for treating diseases or conditions that are characterized by protein aggregation—including some degenerative neurological diseases and conditions, such as Parkinson's disease, Alzheimer's Disease (AD), fronto-temporal dementia (FTD), Lewy body disease (LBD) and Multiple system atrophy (MSA). In one aspect, the compositions of the invention specifically target synuclein, beta-amyloid (e.g., Aβ) and/or tau protein aggregates, and the methods of the invention can be used to specifically prevent, reverse, slow or inhibit synuclein, beta-amyloid and/or tau protein aggregation.

In alternative embodiments, the invention provides isolated, synthetic or recombinant polypeptides or peptides comprising:
(a) (i) a first domain comprising, or consisting of a ligand for a blood brain barrier (BBB) receptor or equivalent; and (ii) a second domain comprising, or consisting of an enzyme or composition that slows the rate of aggregation of a protein aggregate, inhibits the formation of a protein aggregate, or reverses, digests or dissolves a protein aggregate;
(b) the polypeptide or peptide of (a), wherein the first domain comprises a ligand or equivalent for:
 (i) a BBB receptor or equivalent comprising a BB endothelial cell receptor, a low-density lipoprotein (LDL) receptor (LDLR), a low-density lipoprotein receptor-related protein-1 (LRP1), a very-low density lipoprotein receptor (VLDL); or,
 (ii) a transferrin receptor, an insulin growth factor receptor, a megalin receptor and/or an apolipoprotein E receptor 2;
(c) the polypeptide or peptide of (a), wherein the ligand comprises or consists of an apolipoprotein B (ApoB) and/or an apolipoprotein E (ApoE);
(d) the polypeptide or peptide of (a), wherein the second domain comprises:
 (i) a neprilysin (NEP) protein or a secreted neprilysin (NEP) protein (secNEP, a secreted NEP protein), an insulin degrading enzyme (IDE); an endothelin convertase enzyme (ECE), a Serine Endo-Peptidase (SEP, a metalo-endopeptidase), or enzymatically active fragments thereof;
 (ii) an autophagy regulating protein, ATG7 autophagy related 7 homolog (Atg7), a Beclin, a Beclin 1 protein (coiled-coil, myosin-like BCL2 interacting protein), an autophagy-related cysteine endopeptidase 2 isoform A, an autophagy-related cysteine endopeptidase 2 isoform B, an UCHL1, a C54 family autophagy-related protein (e.g., autophagy-related protein APG4 autophagy 4 homolog C isoform 8, or APG4 autophagy 4 homolog C isoform 7), a cysteine protease ATG4D (or autophagy-related protein 4 homolog D), or enzymatically active fragments thereof;
 (iii) an apolipoprotein E (ApoE);
 (iv) a heat shock pathway protein (a Heat shock protein, or HSP), hsp90, hsp84, hsp70, hsp27 or hsp20;
 (v) a protein of the ubiquitin/proteosomal pathway, a ubiquitin, a proteosome, a proteosome 11S regulatory particle, a proteosome 19S particle or a proteosome 20S particle;
 (vi) a protein involved in intracellular clearance of accumulated protein, or a transtherytin (TTR) protein; and/or
 (vii) a protein or nucleic acid that regulates the production of APP, or a Rac1 (Ras-related C3 botulinum toxin substrate 1) protein or an miR-106b family microRNA (microRNAs in the miR-106b family are overexpressed in multiple tumor types and are correlated with the expression of genes that regulate the cell cycle);
(e) the polypeptide or peptide of any of (a) to (d), wherein the protein aggregate comprises or consists of a synuclein, an amyloid beta (Aβ) protein aggregate (e.g., Aβ 1-42) and/or a tau protein aggregate, and/or the protein aggregate comprises a neurofibrillary tangle;
(f) the polypeptide or peptide of any of (a) to (e), wherein the first domain ligand or equivalent specifically binds to:
 (i) a BBB receptor or equivalent comprising a BB endothelial cell receptor, a low-density lipoprotein (LDL) receptor (LDLR), a low-density lipoprotein receptor-related protein-1 (LRP1), a very-low density lipoprotein receptor (VLDL); or,
 (ii) a transferrin receptor, an insulin growth factor receptor, a megalin receptor and/or an apolipoprotein E receptor 2;
(g) the polypeptide or peptide of any of (a) to (f), wherein the second domain comprises a polypeptide or peptide that inhibits protein or peptide aggregation, or dissolves or reverses a protein or peptide aggregation;
(h) the polypeptide or peptide of any of (a) to (g), wherein the protein aggregation comprises or consists of a synuclein, a beta-amyloid (e.g., Aβ 1-42) or a tau protein;
(i) the polypeptide or peptide of any of (a) to (h), wherein the polypeptide or peptide is chemically synthesized or is recombinantly produced, or is a fusion protein or a chemically fused chimeric protein;
(j) the polypeptide or peptide of any of (a) to (i), further comprising a heterologous protein or a non-protein moiety, domain or molecule;
(k) the polypeptide or peptide of any of (a) to (j), further comprising at least one pharmaceutically acceptable excipient; or
(l) the polypeptide or peptide of any of (a) to (k), wherein the polypeptide or peptide comprises an apoB-secNEP (e.g., SEQ ID NO:1), an apoB-Beclin or an apoB-apoE polypeptide.

In one embodiment, the first domain ligand or equivalent comprises or is the equivalent of an antibody or antigen binding fragment that specifically binds to a BB endothelial cell receptor, a low-density lipoprotein (LDL) receptor (LDLR), a low-density lipoprotein receptor-related protein-1 (LRP1), a very-low density lipoprotein receptor (VLDL), a transferrin receptor, an insulin growth factor receptor, a megalin receptor and/or an apolipoprotein E receptor 2.

The invention provides isolated, synthetic or recombinant nucleic acids encoding these hybrid (chimeric) polypeptides of the invention, vectors comprising these nucleic acids, cells comprising the polypeptides and/or nucleic acids of the invention and/or the vectors of the invention; and/or non-human animals comprising the polypeptides and/or nucleic acids of the invention and/or the vectors of the invention, e.g., non-human transgenic animals.

The invention provides pharmaceutical formulations comprising:
(a) at least one polypeptide or peptide of the invention, or
(b) the pharmaceutical formulation of (a), formulated as an aqueous suspension, a solid, a liquid, a powder, an emulsion, a lyophilized powder, a spray, a cream, a lotion, a controlled release formulation, a tablet, a pill, a gel, a liposome, on a patch, in an implant, on a tape, a dragee, a capsule, a lozenge, a gel, a syrup, a slurry and/or a suspension.

The invention provides liposomes comprising at least one polypeptide or peptide of the invention, and/or at least one pharmaceutical composition of the invention.

The invention provides nanoparticles comprising at least one polypeptide or peptide of the invention, and/or at least one pharmaceutical composition of the invention.

The invention provides uses of at least one polypeptide or peptide of the invention, and/or at least one pharmaceutical composition of the invention, for the manufacture of a medicament.

The invention provides uses of at least one polypeptide or peptide of the invention, and/or at least one pharmaceutical composition of the invention, for the manufacture of a medicament for (a) the clearance of a protein or peptide aggregation, or for the treatment, prevention or amelioration of diseases or conditions associated with a protein aggregation; (b) the clearance of a synuclein, beta-amyloid and/or tau protein or peptide aggregation, or preventing, reversing, slowing or inhibiting synuclein, beta-amyloid and/or tau protein aggregation; (c) preventing, reversing, slowing or inhibiting a neurodegenerative disease and/or its symptoms associated with synuclein, beta-amyloid and/or tau protein aggregation; or (d) cleaving an Aβ 1-42 protein.

The invention provides uses of at least one polypeptide or peptide of the invention, and/or at least one pharmaceutical composition of the invention, for the manufacture of a medicament for the treatment, prevention or amelioration of Parkinson's disease (PD), Alzheimer's Disease (AD), Lewy body disease (LBD) or Multiple system atrophy (MSA), and/or any one or several of their symptoms.

The invention provides methods for increasing the clearance of (including e.g. preventing, reversing, slowing or inhibiting) a protein or peptide aggregation, or for the treatment, prevention or amelioration of a disease or a condition (e.g., a neurodegenerative disease or condition), and/or any one or several of their associated symptoms, associated with protein aggregation in an individual comprising administration of an effective amount of at least one polypeptide or peptide of the invention, and/or at least one pharmaceutical composition of the invention, and/or at least one the liposome of the invention, and/or at least one the nanoparticle of the invention. In alternative embodiments, the methods comprise (a) preventing, reversing, slowing or inhibiting synuclein, beta-amyloid and/or tau protein aggregation; or (b) preventing, reversing, slowing or inhibiting a neurodegenerative disease or condition associated with protein aggregation. In alternative embodiments, the disease or condition associated with protein aggregation is Parkinson's disease (PD), Alzheimer's Disease (AD), fronto-temporal dementia (FTD), Lewy body disease (LBD) and/or Multiple system atrophy (MSA).

The invention provides methods for increasing the clearance of (including e.g. preventing, reversing, slowing or inhibiting) a protein or peptide aggregation, or for preventing, inhibiting, reversing or slowing aggregation of a polypeptide or peptide (e.g., a neurotoxic polypeptide or peptide, e.g., a synuclein, beta-amyloid and/or tau polypeptide or peptide), comprising contacting a cell with at least one polypeptide or peptide of the invention, and/or at least one pharmaceutical composition of the invention, and/or at least one the liposome of the invention, and/or at least one the nanoparticle of the invention.

The invention provides methods for increasing the clearance of (including e.g. preventing, reversing, slowing or inhibiting) a protein or peptide aggregation (e.g., a neurotoxic polypeptide or peptide, e.g., a synuclein, beta-amyloid and/or tau polypeptide or peptide), or for preventing, inhibiting, reversing or slowing a neurodegenerative process, a disease or a condition, and/or any one or several of their associated symptoms, to an individual in need thereof, comprising (a) administering to the individual at least one polypeptide or peptide of the invention, and/or at least one pharmaceutical composition of the invention, and/or at least one the liposome of the invention, and/or at least one the nanoparticle of the invention;

(b) the method of (a), wherein the administration comprises contacting a nerve cell or a CNS tissue with at least one polypeptide or peptide of the invention, and/or at least one pharmaceutical composition of the invention, and/or at least one the liposome of the invention, and/or at least one the nanoparticle of the invention; or (c) the method of (a) or (b), wherein the contacting is in vitro, ex vivo or in vivo.

The invention provides methods for increasing the clearance of (including e.g. preventing, reversing, slowing or inhibiting) a protein or peptide aggregation, or interfering in the accumulation of protein or peptide aggregation (e.g., a neurotoxic polypeptide or peptide, e.g., a synuclein, beta-amyloid and/or tau polypeptide or peptide) in a cell (e.g., a nerve or a CNS cell), or reversing protein or peptide aggregation in a cell (e.g., a nerve or a CNS cell), or preventing protein or peptide aggregation in a cell (e.g., a nerve or a CNS cell), comprising:

(a) contacting the cell with an effective amount of at least one polypeptide or peptide of the invention, and/or at least one pharmaceutical composition of the invention, and/or at least one the liposome of the invention, and/or at least one the nanoparticle of the invention; or (b) the method of (a), wherein the contacting is in vitro, ex vivo or in vivo. The CNS cell can be any cell in the central nervous system, including nerve or non-nerve cells, e.g., cells such as glial cells, including microglia (e.g., macrophages) or macroglial cells, e.g., ependymal cells, radial cells, oligodendrocytes, astrocytes, Schwann cells and the like.

The invention provides kits comprising at least one polypeptide or peptide of the invention, and/or at least one pharmaceutical composition of the invention, and/or at least one the liposome of the invention, and/or at least one the nanoparticle of the invention. In alternative embodiments the kits of the invention further comprise instructions for using the polypeptide or peptide, pharmaceutical composition, liposome or nanoparticle; where in one embodiment the instructions comprise how to practice a method or use of this invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The following drawings are illustrative of aspects of the invention and are not meant to limit the scope of the invention as encompassed by the claims.

FIG. 3A (upper PAGE gel panel) illustrates neprilysin protein as detected by Western blot (A); FIG. 3B (middle PAGE gel panel) illustrates analysis of activity against a N-terminal FITC tagged Aβ protein (B); and as illustrated in FIG. 3C (lower PAGE gel panel) to ensure equal loading actin was analyzed in the protein samples (C); and as graphically illustrated in FIG. 3D (i.e., the lower two panels or graphs), total neprilysin was quantified (by pixel intensity) and the N-terminal cleavage product (by pixel intensity) was quantified to analyze neprilysin activity (D)—the left panel graphically illustrates neprilysin protein activity and the right panel graphically illustrates Aβ cleavage product production, as discussed in Example 1, below.

Like reference symbols in the various drawings indicate like elements.

DETAILED DESCRIPTION

Figure 1:
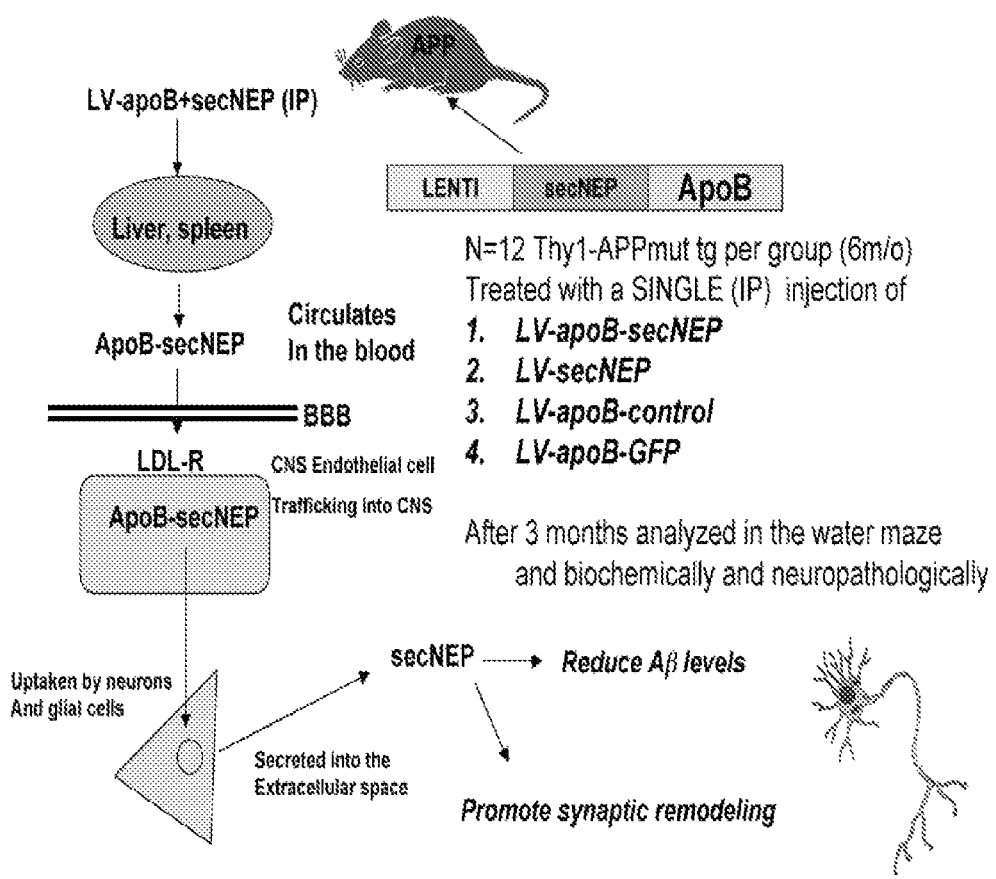
FIG. 1 illustrates a diagrammatic representation of an exemplary mode of action of the invention and in vivo proof of concept experiment in an APP tg model of AD pathology, as discussed in Example 1, below.

In alternative embodiments, the invention provides novel approaches to the treatment, amelioration, reversal and/or prevention of a degenerative neurological disease characterized by a protein aggregation, such as Parkinson's disease, Alzheimer's Disease (AD), fronto-temporal dementia (FTD), Lewy body disease (LBD) and/or Multiple System Atrophy (MSA). In alternative embodiments, compositions and methods of the invention are used to treat, prevent, reverse (partially or completely) and/or ameliorate, including ameliorating symptoms and/or delaying progression of the disease, after diagnosis (tentative or definitive) and/or one or more diagnostic symptoms have become apparent or are otherwise detected.

In one embodiment, compositions and methods of the invention are used to reverse and/or prevent the formation of a protein aggregate, e.g., a neurofibrillary tangle or an aggregrate comprising a tau protein, an amyloid protein or fragment (e.g., Aβ, such as the Aβ 1-42 fragment) or a synuclein protein; for example, compositions and methods of the invention can be used to decrease the rate of formation of protein aggregates, e.g., neurofibrillary tangles, or to clear or dissolve them; wherein in one embodiment this can reverse, slow and/or prevent cell (e.g., neuron and/or CNS cell) damage, including damage associated with the destruction or impairment of cognitive function.

In one embodiment, compositions and methods of the invention reverse or prevent the (non-normal) accumulation of or aggregation of synuclein, tau and/or amyloid-beta (Aβ) (e.g., Aβ 1-42) protein, which can be the result of an imbalance in the synthesis, aggregation and clearance of the protein prior to the formation of an insoluble tangle or other pathological or toxic protein aggregation. In alternative embodiments, the invention provides specific polypeptides that can be delivered peripherally (directly, indirectly and/or via gene therapy) and cross the blood-brain barrier, or that are delivered directly into the CNS.

In alternative aspects, the compositions and methods of the invention are used to specifically target tau, amyloid (including amyloid-beta (Aβ), such as Aβ 1-42) and/or synuclein aggregation. While the invention is not limited by any particular mechanism of action, amyloid-beta or synuclein aggregation is thought to be caused by a mis-alignment of the protein early in the disease process, which permits the formation of protein multimers due to head-to-head aggregation; as the monomer units increase, the aggregated proteins can take on a pore-like shape, which can embed in the membrane of the neuron, disrupting ion flow and homeostasis of the cell. While the invention is not limited by any particular mechanism of action, in alternative aspects, the compositions and methods of the invention are used to prevent tau, amyloid (including amyloid-beta (Aβ), e.g., Aβ 1-42) and/or synuclein aggregated proteins from taking on a pore-like shape that can disrupt ion flow and homeostasis.

The invention also provides methods comprising use of compositions of this invention for testing the efficacy of compositions, including small molecules and/or peptides, to block, reverse or inhibit protein, e.g., tau, amyloid-beta (Aβ), e.g., Aβ 1-42, or synuclein, aggregation in an in-vitro (cell free) system and in a neuronal cell line; assays have been conducted for aggregation, growth and survival of cells. The small molecules and/or peptides can be tested in synuclein (Syn) transgenic (Tg) mice.

Generating and Manipulating Nucleic Acids

In alternative aspects, the invention provides, e.g., isolated, synthetic and/or recombinant nucleic acids encoding the hybrid (chimeric) polypeptides of this invention (and their complementary sequences). The nucleic acids of the invention can be made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., encoding the hybrid (chimeric) polypeptides of this invention) generated from these nucleic acids can be individually isolated or cloned and tested for a desired activity. Any recombinant expression system can be used, including bacterial, fungal, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the invention is to clone from genomic samples, and, if desired, screen and re-clone inserts isolated or amplified from, e.g., genomic clones or cDNA clones. Sources of nucleic acid used to practice the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The invention provides and uses fusion proteins and nucleic acids encoding them. A polypeptide used to practice this invention (e.g., a fusion protein for increasing the clearance of protein aggregates or reversing aggregation of proteins) can be fused to a heterologous peptide or polypeptide, such as a peptide for targeting an inhibitory compound used to practice this invention; or the heterologous or chimeric peptide or polypeptide can be an N-terminal identification peptide which imparts a desired characteristic, such as fluorescent detection, increased stability and/or simplified purification.

Peptides and polypeptides used to practice this invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice this invention can be an oligonucleotide, nucleotide, polynucleotide, or a fragment of any of these, comprising DNA or RNA of natural (e.g., genomic) or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been de-phosphorylated.

In alternative aspects, compounds used to practice this invention include genes or any segment of DNA involved in producing a polypeptide (e.g., a chimeric/hybrid polypeptide of this invention); it can include regions preceding and following the coding region (leader and trailer) as well as, where applicable, intervening sequences (introns) between individual coding segments (exons). "Operably linked" can refer to a functional relationship between two or more nucleic acid (e.g., DNA, RNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system.

In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequence used to practice this invention, which can be capable of affecting expression of the nucleic acid, e.g., a structural gene or a transcript (e.g., encoding a chimeric/hybrid polypeptide of this invention) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector" (e.g., expression vector or expression cassette) used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure (e.g., as an episomal entity), or can be incorporated (e.g., stably integrated) within the host's genome.

In alternative aspects, "promoters" used to practice this invention include all sequences capable of driving transcription of a coding sequence in a cell, e.g., a mammalian cell such as a brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

Constitutive promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions. Examples of environmental conditions that may affect transcription by inducible promoters used to practice this invention include the presence of an inducing factor administered to a subject. "Tissue-specific" promoters used to practice this invention can be transcriptional control elements that are only active in particular cells or tissues or organs, e.g., in a nerve, CNS, glial (e.g., a microglia cell, a macrophage, a macroglial cell, an ependymal cell, a radial cell, an oligodendrocyte, an astrocyte or a Schwann cell) or brain cell. Tissue-specific regulation may be achieved by certain intrinsic factors that ensure that genes encoding proteins specific to a given tissue, e.g., brain, are expressed.

Polypeptides and Peptides

In alternative embodiments, the invention provides polypeptides and peptides comprising: a first domain comprising, or consisting of a ligand for a blood brain barrier (BBB) receptor; and, a second domain comprising, or consisting of an enzyme or composition that slows the rate of aggregation of a protein aggregate, inhibits the formation of a protein aggregate, or reverses, digests or dissolves a protein aggregate.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) including any automated polypeptide synthesis process known in the art.

The peptides and polypeptides used to practice the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

In alternative embodiments, compositions used to practice the invention comprise an oligopeptide, peptide, polypeptide, or protein sequence, or to a fragment, portion, or subunit of any of these and to naturally occurring or synthetic molecules. In alternative aspects, polypeptides used to practice the invention comprise amino acids joined to each other by peptide bonds or modified peptide bonds and may comprise modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide.

In alternative embodiments, a polypeptide used to practice the invention can have one or more of many types of modifications, e.g., modifications including acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, phosphorylation, prenylation, racemization, selenoylation, sulfation and transfer-RNA mediated addition of amino acids to protein such as arginylation. See for example, Creighton, T. E., Proteins—Structure and Molecular Properties 2nd Ed., W.H. Freeman and Company, New York (1993); *Posttranslational Covalent Modification of Proteins*, B. C. Johnson, Ed., Academic Press, New York, pp. 1-12 (1983)).

In alternative embodiments, peptides and polypeptides used to practice the invention can comprise any "mimetic" and/or "peptidomimetic" form. In alternative embodiments, peptides and polypeptides used to practice the invention can comprise synthetic chemical compounds which have substantially the same structural and/or functional characteristics of natural polypeptides. The mimetic used to practice the invention can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. Routine experimentation will determine whether a mimetic is effective for practicing the invention; e.g., increasing the clearance of protein aggregates such as tau, synuclein and/or amyloid beta protein (Aβ) aggregates.

Polypeptide mimetic compositions for practicing the invention can comprise any combination of non-natural structural components. In alternative aspects, mimetic compositions for practicing the invention can comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., $-C(=O)-CH_2-$ for $-C(=O)-NH-$), aminomethylene ($CH_2-NH$), ethylene, olefin ($CH=CH$), ether ($CH_2-O$), thioether ($CH_2-S$), tetrazole ($CN_4-$), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY). A polypeptide can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, e.g., under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics that can be used include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Polypeptides used to practice this invention can comprise signal sequences, i.e., leader sequences, e.g., for secreting a chimeric/hybrid polypeptide of the invention, or a recombinant antibody used to practice the invention, from a production host cell.

Antibodies

In alternative embodiments, the first domain ligand or equivalent of a polypeptide or peptide of the invention comprises or is the equivalent of an antibody that specifically binds to a BB endothelial cell receptor, a low-density lipoprotein (LDL) receptor (LDLR), a low-density lipoprotein receptor-related protein-1 (LRP1), a very-low density lipoprotein receptor (VLDL), a transferrin receptor, an insulin growth factor receptor, a megalin receptor and/or an apolipoprotein E receptor 2. In alternative aspects, an antibody or fragment for practicing the invention can comprise a peptide or polypeptide capable of specifically binding to an epitope of any of these proteins, see, e.g. Fundamental Immunology, Third Edition, W. E. Paul, ed., Raven Press, N. Y. (1993); Wilson (1994) J. Immunol. Methods 175:267-273; Yarmush (1992) J. Biochem. Biophys. Methods 25:85-97. In alternative aspects, an antibody or fragment thereof for practicing the invention includes antigen-binding portions, i.e., "antigen binding sites," (e.g., fragments, subsequences, complementarity determining regions (CDRs)) that retain capacity to bind antigen (e.g., a BB endothelial cell receptor protein, or immunogenic fragments thereof) including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

In alternative embodiments, antibodies or antigen binding fragments thereof used to practice this invention comprise "affinity matured" antibodies, e.g., antibodies or antigen binding fragments comprising with one or more alterations in one or more hypervariable regions which result in an improvement in the affinity of the antibody or antigen binding fragment for antigen; e.g., a BB endothelial cell receptor protein, or immunogenic fragments thereof. In alternative embodiments, antibodies or antigen binding fragments used to practice this invention are matured antibodies or antigen binding fragments having nanomolar or even picomolar affinities for the target antigen, e.g., a targeted transcriptional activating factor. Affinity matured antibodies or antigen binding fragments can be produced by procedures known in the art.

Pharmaceutical Compositions

The invention provides compositions as described herein, including pharmaceutical compositions, e.g., in the manufacture of medicaments for preventing, reversing, slowing or inhibiting protein aggregation, e.g., for treating diseases or conditions that are characterized by protein aggregation—including degenerative neurological diseases such as Parkinson's disease, Alzheimer's Disease (AD), fronto-temporal dementia (FTD), Lewy body disease (LBD) and Multiple system atrophy (MSA).

In alternative embodiments, the compositions (e.g., hybrid or chimeric polypeptides) of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions (e.g., hybrid polypeptides) of the invention include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents of the invention, including compositions (e.g., hybrid polypeptides) of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann, Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see e.g., U.S. Pat. No. 6,689,118 or 6,569,143; Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities, body weight, and the like, in accordance with the particular mode of administration selected and the patient's needs.

For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

Nanoparticles and Liposomes

The compositions and formulations of the invention can be delivered by the use of liposomes. By using liposomes, particularly where the liposome surface carries ligands specific for target cells, or are otherwise preferentially directed to a specific organ or cell type, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The invention also provides nanoparticles and liposomal membranes comprising compounds of this invention which target specific molecules, including biologic molecules, such as polypeptide, including cell surface polypeptides. Thus, in alternative embodiments, the invention provides nanoparticles and liposomal membranes targeting BBB cells, such as BBB endothelial cells, or nerve or glial cells (e.g., microglia, macrophage, macroglial, ependymal, radial, oligodendrocyte, astrocyte or Schwann cells), including dysfunctional cells or cells affected by an intracellular or extracellular protein aggregation.

In alternative embodiments, the invention provides nanoparticles and liposomal membranes comprising (in addition to comprising compounds of this invention) molecules, e.g., peptides or antibodies, that selectively or specifically target BBB cells, such as BBB endothelial cells, or nerve or glial cells, or diseased, infected, dysfunctional and/or normal nerve or glial cells. In alternative embodiments, the invention provides nanoparticles and liposomal membranes to targeted receptors on BBB cells, such as BBB endothelial cells, or nerve or glial cells. See, e.g., U.S. patent application publication no. 20060239968.

Thus, in one aspect, the compositions of the invention are specifically targeted for BBB cells, such as BBB endothelial cells.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to BBB cells, such as BBB endothelial cells, or nerve or glial cells, in patients suffering from a diseases or condition as described herein, e.g., such as an individual with a degenerative neurological disease related to or caused by protein aggregation, e.g., synuclein, beta-amyloid and/or tau protein aggregation.

The invention also provides multilayered liposomes comprising compounds of this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds of this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

For example, in one embodiment, compositions and formulations of the invention are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations of the invention are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937 Amphoteric liposomes of the invention can comprise an active ingredient and at least one amphipathic cationic lipid, at least one amphipathic anionic lipid, and at least one neutral lipid, e.g., as described in U.S. Pat. No. 7,371,404.

In another embodiment, compositions and formulations of the invention are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations of the invention are delivered by the use of liposomes comprising glycerides, glycerophospholipids, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

In one embodiment, compositions and formulations of the invention are delivered by the use of liquid-crystalline multimolecular aggregates comprising a plurality of amphiphilic molecules dispersed in an aqueous solution, e.g., as described in U.S. Pat. No. 7,368,129.

In one embodiment, compositions and formulations of the invention are delivered to the respiratory tract of an individual via inhalation, e.g., using a nebulized liposomal aerosol, e.g., comprising a dilauroylphosphatidylcholine liposome, e.g., as described in 7,348,025.

In one embodiment, compositions and formulations of the invention are delivered via their formulation into a unimolecular multi-arm block copolymer comprising, e.g., a hydrophilic polymer segment such as poly(alkylene glycols), copolymers of ethylene glycol and propylene glycol, poly (olefinic alcohol), poly(vinylpyrrolidone), poly(hydroxyalkylmethacrylamide), poly(hydroxyalkylmethacrylate), poly(saccharides), poly(.alpha.-hydroxy acid), poly(vinyl alcohol), polyphosphazene, polyoxazoline and poly(N-acryloylmorpholine), and the like, e.g., as described in U.S. Pat. App. Pub. No. 20080069902.

In one embodiment, compositions and formulations of the invention are delivered via solid, biodegradable in-situ implants; e.g., by administering a liquid pharmaceutical composition comprising an effective amount of a biocompatible, water-insoluble, biodegradable polymer and an effective amount of a peptide or polypeptide of this invention. In one aspect, a peptide or polypeptide of this invention covalently modified with one or more lipophilic or amphiphilic moieties, which are dissolved or dispersed in a biocompatible, water-soluble organic solvent, e.g., as described in U.S. Pat. App. Pub. No. 20080020016. Compositions and formulations of the invention can be delivered using any injectable liquid biodegradable polymeric composition, e.g., as an in situ forming implant to deliver a peptide or polypeptide of this invention, e.g., as described in U.S. Pat. Nos. 6,565,874; 6,528,080; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; 5,278,201; 4,938,763.

In one embodiment, compositions and formulations of the invention are delivered via transdermal systems for sustained delivery, e.g., as described in U.S. Pat. App. Pub. No. 20070287949, Levin et al. For example, compositions and formulations of the invention can be delivered via transdermal patches, and/or via an apparatus that generates microchannels in the skin of a subject in combination with a transdermal patch, see e.g., Levin et al.

In one embodiment, compositions and formulations of the invention are delivered via orally administered formulations, e.g., as described in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

Therapeutically Effective Amount and Dose

The compositions and formulations of the invention can be administered for prophylactic and/or therapeutic treatments for any degenerative neurological disease such as Parkinson's disease (PD), Alzheimer's Disease (AD), fronto-temporal dementia (FTD), Lewy body disease (LBD) and Multiple system atrophy (MSA), and/or any one or several of symptoms related to these diseases or conditions. In therapeutic applications, in alternative embodiments, compositions are administered to a subject already suffering from a condition, infection or disease in an amount sufficient to cure, alleviate or partially arrest the clinical manifestations of the condition, infection or disease and its complications (a "therapeutically effective amount"). In alternative embodiments of the methods of the invention, a pharmaceutical composition is administered in an amount sufficient to treat, prevent, reverse (partially or completely) or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent, reverse (partially or completely) or ameliorate (including slowing the progression of) Parkinson's disease, Alzheimer's Disease (AD), fronto-temporal dementia (FTD), Lewy body disease (LBD) and Multiple system atrophy (MSA), and/or any one or several of symptoms related to these diseases or conditions.

The amount of pharmaceutical composition of the invention adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Droning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively prevent, reverse, slow or inhibit a degenerative neurological disease related to or caused by protein aggregation, e.g., synuclein, beta-amyloid and/or tau protein aggregation, such as Parkinson's disease, Alzheimer's Disease (AD), fronto-temporal dementia (FTD), Lewy body disease (LBD) and Multiple system atrophy (MSA). For example, an exemplary pharmaceutical formulation for oral administration of a hybrid/chimeric polypeptide or peptidomimetic of the invention is in a daily amount of between about 0.1 to 0.5 to about 10, 20, 30, 40, 50, 60, 70, 80, 90, 100 or 1000 or more ug per kilogram of body weight per day. In an alternative embodiments, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

Initiation and Assessment of Efficacy of Therapy

In alternative embodiments, compositions of this invention are used to treat dementia and dementia-type disorders related to protein aggregation, and any systems and/or methods for analyzing and assessing dementia and dementia-type disorders can be used to assess the efficacy of a composition of this invention on an individual, e.g., to determine and calibrate a dose or a dosage regimen; for example, by integrating the use of electroencephalography (EEG), neuropsychological or cognitive testing data, and cardiovascular risk factor data. In practicing this invention, systems and methods for early detection of dementia, including Alzheimer's disease (AD), Parkinson's disease (PD), vascular dementia (VAD), mixed dementia (AD and VAD), MCI, and other dementia-type disorders can be used. Accurate detection of mild dementia and some cases of mild cognitive impairment in addition to the detection of moderate to severe dementia can be assessed using any method or protocol, e.g., as described in U.S. Pat. App. Pub. No. 20070299360.

Any cognitive and/or clinical chemistry of imaging test or combination thereof can be used to tentatively diagnose AD, PD, VAD and the like, or predict the likelihood of an individual being disposed to getting or having AD, PD, VAD and the like, and thus trigger the initiation of therapy comprising use of compositions and methods of this invention. For example, elevated levels of tau and/or A$\beta$ protein in the CNS, e.g., in cerebro-spinal fluid, can be sufficient to thus trigger the initiation of therapy comprising use of compositions and methods of this invention; e.g., as described in U.S. Pat. No. 5,397,712, which describes use of immunoassays to diagnosis Alzheimer's disease. Tests indicating impaired cognition, or mild cognitive impairment or MCI, can trigger the initiation of therapy comprising use of compositions and methods of this invention; e.g., as described in U.S. Pat. No. 6,964,638, or U.S. Pat. No. 6,280,198, describing use of a computer for giving a series of cognitive dysfunction tests to an individual. Results from imaging tests, e.g., MRI or ultrasound imaging, can be used to trigger the initiation of therapy comprising use of compositions and methods of this invention; e.g., as described in U.S. Pat. No. 6,875,176, describing methods for noninvasively inducing a detectable tissue displacement at a central nervous system (CNS) target tissue site by applying an ultrasound pulse; noninvasively determining the induced tissue displacement at or in proximity to the CNS target tissue site; and relating the induced tissue displacement with a physiological property of the CNS target tissue.

Another test that can be used to determine when to initiate a treatment or a prophylactic therapy comprising use of compositions and methods of this invention is described in U.S. Pat. No. 7,335,652, which described methods for determining the stage of neurofibrillary degeneration associated with a tauopathy in a subject-aggregated paired helical filament (PHF) tau proteins are labeled. The tauopathy can be imaged in vivo, e.g., by positron emission tomography (PET).

Any test or assessment, e.g., as those described above, that can trigger the initiation of a therapy comprising use of compositions and methods of this invention also can be used to monitor the success of a treatment regimen of this invention; e.g., a dosage, frequency of administration, formulation or route of administration can be adjusted by one of skill in the art during the course of a therapeutic or prophylactic treatment comprising use of a composition or method of this invention.

Genetic markers of risk toward Alzheimer's disease (AD) also can be used to assess when to begin treatments comprising use of compositions and methods of this invention; such genetic markers include e.g. mutations in the APP gene such as mutations at position 717 and positions 670 and 671, referred to as the Hardy and Swedish mutations. Early-onset AD, also called familial AD (FAD), can be inherited. FAD can be caused by a number of different gene mutations, e.g., on chromosomes 21, 14, and 1; these mutations may cause abnormal proteins and protein aggregates to be formed. Mutations on chromosome 21 may cause the formation of abnormal amyloid precursor protein (APP). A mutation on chromosome 14 may cause abnormal presenilin 1 to be made, and a mutation on chromosome 1 may lead to abnormal presenilin 2.

A predisposing genetic risk factor in late-onset AD may indicate an increase in a person's risk of developing the disease—thus triggering initiation of use of a composition or method of this invention. For example, in one embodiment, this increased risk is associated with the apolipoprotein E (APOE) gene found on chromosome 19. APOE comes in several different alleles, where APOE $\epsilon$2, APOE $\epsilon$3, and APOE $\epsilon$4 occur most frequently. APOE $\epsilon$2 is relatively rare and may provide some protection against the disease. If AD does occur in a person with this allele, it develops later in life than it would in someone with the APOE ε4 gene. APOE ε3 is the most common allele. It may plays a neutral role in AD. APOE ε4 occurs in about 40 percent of all people who develop late-onset AD and is present in about 25 to 30 percent of the population. People with AD are more likely to have an APOE ε4 allele than people who do not develop AD.

Other markers of risk for AD are mutations in the presenilin genes, PS1 and PS2, and ApoE4, family history of AD, hypercholesterolemia or atherosclerosis, to name just a few.

Drug Combinations and Co-Administrations

The compositions and formulations of the invention can further comprise other drugs or pharmaceuticals, e.g., other compositions for treating or palliative for a degenerative neurological disease related to or caused by protein aggregation, e.g., synuclein, beta-amyloid and/or tau protein aggregation, e.g., fronto-temporal dementia (FTD), Parkinson's disease, Alzheimer's Disease (AD), Lewy body disease (LBD), a hereditary systemic amyloidosis and/or Multiple system atrophy (MSA) and related symptoms or conditions. For example, the methods and/or compositions and formulations of the invention can be co-formulated with and/or co-administered with antibiotics (e.g., antibacterial or bacteriostatic peptides or proteins), e.g., those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

The compositions and formulations of the invention can be co-administered with another therapeutic or prophylactic therapy or therapeutic agent, e.g., for an Alzheimer's disease, a Parkinson's disease, a hereditary systemic amyloidosis etc., including treatment or palliative drugs such as an antibody to Aβ peptide (see e.g., U.S. Pat. No. 6,913,745), tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl] ethyl]-6H-pyrrolo-[4,5-f-]-1,2-benzisoxazol-6-one maleate), ER-127528 (4-[5,6-dimethoxy-2-fluoro-1-indanon)-2-yl] methyl-1-(3-fluorobenzyl)pipe-ridine hydrochloride), zanapezil (TAK-147; 3-[1-(phenylmethyl)piperidin-4-yl]-1-(2,3, 4,5-tetrahydro-1H-1-benzazepin-8-yl)-1-propane fumarate), Metrifonate (T-588; (−)-R-.alpha.-[[2-(dimethylamino) ethoxy]methyl]benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz [b,f]oxepine-10-methanamine), SDZ-220-581 ((S)-.alpha.-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyr-idine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and/or Minozac (2-(4-(4-methyl-6-phenylpyridazin-3-yl)piperazin-1-yl)pyrimidine dihydrochloride hydrate).

Kits

The invention provides kits comprising compositions (including the pharmaceutical compositions and formulations) of this invention and methods of the invention, instructions (regarding the methods of the invention to treat, prevent, reverse (partially or completely) or ameliorate (including slowing the progression of) degenerative neurological diseases related to or caused by aggregation, e.g., synuclein, beta-amyloid and/or tau protein aggregation), or any combination thereof. As such, kits, nanoparticles and the like are provided herein.

The invention will be further described with reference to the following examples; however, it is to be understood that the invention is not limited to such examples.

EXAMPLES

Example 1

Targeting Polypeptides to the CNS for Clearance of Aggregated Proteins

This example presents data demonstrating that exemplary compounds of this invention are effective in accelerating protein aggregation removal from the CNS.

While the invention is not limited by any particular mechanism of action, abnormal accumulation of proteins in the CNS can cause or aggravate neurodegenerative disease. Aβ is a 40-42 amino acid long peptide derived from the proteolysis of amyloid precursor protein (APP) by the gamma and beta-secretases. Abnormal accumulation amyloid beta protein (Aβ) and tau in the nervous system results in progressive damage to neurons leading to Alzheimer's Disease (AD) and fronto-temporal dementia (FTD). These devastating disorders affect over 5 million people in the US alone.

In alternative aspects, administration of compositions of this invention can prevent or reverse the accumulation of oligomeric forms of Aβ proteins which promote nerve degeneration by damaging the synaptic connections among neurons. In AD, accumulation of Aβ oligomers is the results of alterations in the balance between the rate of Aβ synthesis, aggregation and clearance. Although most recent therapies for AD have been focused at blocking synthesis of aggregation of Aβ relatively less has been done to promote clearance. The clearance of Aβ depends on removal by: i) chaperones (e.g.: apoE, beta-2M, HSP's), ii) degrading enzymes (e.g.: neprilysin (NEP), IDE, EDE), iii) non-lysosomal degradation (e.g.: proteosome) and lysosomal degradation (e.g.: autophagy, e.g., Beclin).

In one embodiment, practicing the compositions and methods of this invention increases the clearance of Aβ by delivering specific hybrid polypeptides that selectively traffic into the CNS and target Aβ for degradation (FIG. 1). In alternative embodiments, the hybrid polypeptides of this invention can be synthesized by recombinant technologies and delivered intravascularly or by gene therapy.

In one embodiment, a vector, e.g., a viral vector, containing the gene sequence for the fusion protein of interest can be administered by intraperitoneal (IP) injection. In one embodiment, a vector, e.g., a viral vector, drives the production of the fusion polypeptide in a tissue in vivo, e.g., in a peripheral organ or organs (e.g., liver and spleen), as illustrated in FIG. 1. This embodiment allows the trafficking of these specific hybrid polypeptides into the CNS because of the fusion with a fragment of the apoB protein. We show data from our work on the treatment of AD with the exemplary hybrid polypeptide of the invention apoB-secNEP. However the invention provides a number of additional polypeptides to reduce accumulation of Aβ, including the hybrid polypeptides apoB-secNEP, apoB-Beclin and apoB-apoE.

In one embodiment, the invention provides therapies for AD and related neurodegenerative disorders by increasing the clearance of toxic Aβ aggregates via exogenous delivery of hybrid polypeptides with the ability of crossing the blood brain barrier (BBB).

In one embodiment, this invention provides molecules that act in AD by direct injection into the CNS. In one embodiment, this invention provides a peripherally administered therapy that can penetrate into the CNS and increase the clearance of Aβ aggregates. In one embodiment, this invention provides a peripherally administered therapy that allows the trafficking of peripherally administered hybrid polypeptides or equivalent gene vectors into the CNS. In one embodiment, these hybrid polypeptides selectively activate clearance pathways that remove Aβ aggregates, therefore reducing the neuronal damage. In alternative embodiments, the invention combines the use of the apoB peptide with polypeptides that promote the clearance of Aβ aggregates for the treatment of AD and related disorders.

In alternative embodiments, the invention provides therapeutic approaches for AD and related disorders focused at the clearance of Aβ aggregates. In alternative embodiments, the invention provides approaches for increasing clearance of Aβ by the administration of a polypeptide of the invention or the administration of a gene vector of the invention without need for its direct injection or insertion into the brain. This indirect administration allows relatively large molecules to enter into the CNS when administered peripherally.

In alternative embodiments, the invention also provides use of conventional constructs expressing hybrid compositions of this invention, e.g., NEP and other Aβ-degrading enzymes, administered peripherally and/or injected directly into the brain.

In alternative embodiments, the invention provides compositions for crossing the BBB, these compositions comprising fusion proteins using the TAT sequence of HIV, ferritin and other carrier molecules. In alternative embodiments, the invention provides compositions for crossing the BBB comprising highly efficient hybrid fusion polypeptide expressing Aβ degrading enzymes to enter the CNS and reduce protein aggregation, including ameliorating AD-associated pathology.

In alternative embodiments, the invention provides compositions, or constructs, comprising two basic components, a fragment of ApoB or equivalent which allows trafficking into the CNS and a protein aggregate degrading enzyme of interest, e.g., an Aβ degrading enzyme of interest (e.g., NEP).

In alternative embodiments, the invention provides novel strategies and methods for delivery of the compositions of this invention. In alternative embodiments, the invention is used for targeted, personalized medicine, to provide for the directed, focused administration of a therapeutic strategy that targets the degradation of aggregated protein, e.g., Aβ, by the specific biochemical action that degrades it in nature.

In alternative embodiments, the invention is used to complement other therapeutic strategies being developed to treat degenerative neurological diseases such as Parkinson's disease (PD), Alzheimer's Disease (AD), fronto-temporal dementia (FTD), Lewy body disease (LBD), a hereditary systemic amyloidosis and/or Multiple system atrophy (MSA). For example, compositions and methods of this invention can be used with any vaccine against Aβ and/or the use of molecules to dissociate the aggregation, providing a full three pronged approach to AD treatment, by stopping Aβ synthesis, by blocking Aβ aggregation and by enzymatic clearance of these toxic peptides.

In alternative embodiments, the invention provides biological therapies for degenerative neurological diseases such as PD, AD and the like, that are capable to transit a therapeutic composition of this invention across the BBB into the CNS; in alternative embodiments the invention based on the concept of utilizing hybrid proteins comprising part of an apoB sequence linked to Aβ clearing agents.

In alternative embodiments, the invention provides means to overcome the BBB control of the passage of substances from the blood into the central nervous system. In alternative embodiments, the invention provides a treatment of brain disorders that overcomes the impediment of delivery of therapeutic macromolecules to the brain.

In alternative embodiments, the invention provides for vascular distribution of a therapeutic protein of this invention. In alternative embodiments, the invention targets any well-characterized BBB receptor, including a low-density lipoprotein receptor, transferrin receptor, and/or insulin growth factor receptor. In alternative embodiments, the invention can use any member of the low-density lipoprotein receptor family, which is a group of cell surface receptors that bind lipoprotein complexes for internalization to the lysosomes.

In alternative embodiments, the invention can use any one of ten different receptors, e.g., a low-density lipoprotein receptor (LDLR), a low-density lipoprotein related receptor (LRP), a very-low density lipoprotein receptor (VLDL), a megalin and/or an apolipoprotein E receptor 2.

In alternative embodiments, the compositions of the invention bind to receptors expressed in a tissue specific manner, e.g., bind to receptors that bind (have as ligands) apolipoprotein complexes, e.g., including apolipoproteins such as apolipoprotein B (ApoB) and apolipoprotein E (ApoE), function to bind lipids in the blood stream and target them for lysosomal degradation. In alternative embodiments, the compositions of the invention comprise apolipoproteins or their fragments that bind to their respectively receptors, e.g., an LDL receptor, on the cell surface of a targeted cell, wherein then the complex is endocytosed. While the invention is not limited by any particular mechanism of action, conversion to an early endosome and subsequent lowering of the compartmental pH, results in release of the compositions of the invention (e.g., comprising the apolipoprotein) and recycling of the receptor to the cell surface. While the invention is not limited by any particular mechanism of action, at the BBB, LDLR binds compositions of the invention (e.g., comprising the apolipoprotein), resulting in transcytosis to the abluminal side of the BBB where the compositions of the invention (e.g., comprising the apolipoprotein) are released to be taken up by neurons and/or astrocytes.

We have shown that the addition of the apolipoprotein B LDL receptor-binding domain to a lysosomal enzyme such as glucocerebrosidase could target the enzyme for passage across the BBB and uptake into neurons and astrocytes (see reference 1, below). The protein was subsequently shown to target to the lysosomes of these cells.

Figure 2:
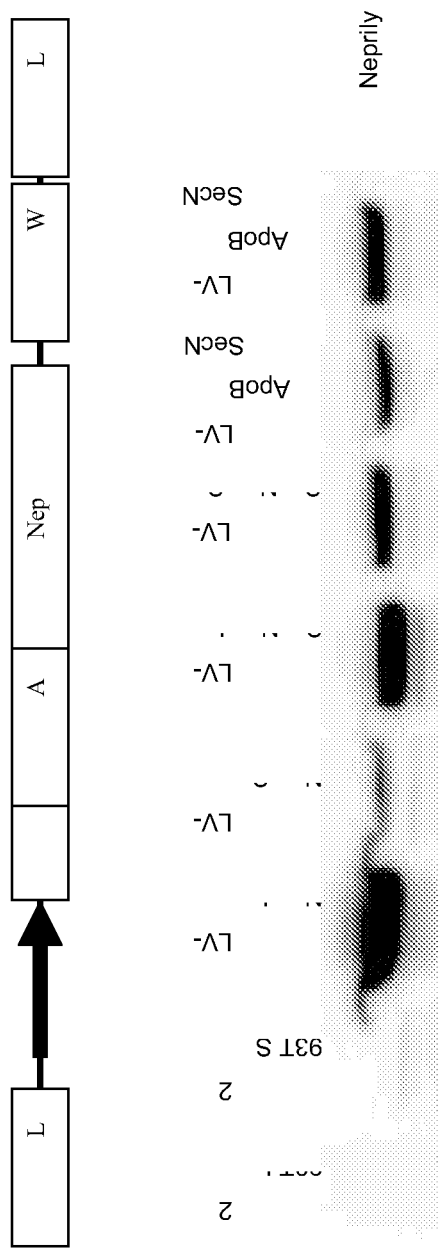
FIG. 2 illustrates expression of neprilysin ("Nep") from an exemplary expression construct of this invention comprising a lentivirus vector ("LV"): the upper panel illustrates how a hybrid or chimeric nucleic acid construct of this invention—a ApoBSecNep construct—was cloned into a $3^{rd}$ generation lentivirus vector containing the CMV promoter (arrow) and the WPRE element (Woodchuck Hepatitis Virus (WHV) Posttranscriptional Regulatory Element) to aid transcription of the gene; the lower panel illustrates a protein analysis of cell lysates and supernatant from 293T cells infected with this exemplary expression construct, where proteins isolated from the cells are blotted and probed for the neprilysin ("N") protein, as discussed in Example 1, below.

Data in this Example demonstrate that compositions and methods of this invention can deliver the exemplary Aβ degrading enzyme, NEP utilizing the invention's method of delivering proteins to the CNS by passage across the BBB. Specifically, we developed a secreted NEP protein (NEP is also known as neprilysin, membrane metallo-endopeptidase, neutral endopeptidase, CD10) (secNEP) that was fused at the N-terminus peptide of ApoB (FIG. 2). This relies on the addition of the secretory signal and the ApoB leader sequence to NEP. We have previously shown (e.g., reference 1, below) that this apoB peptide facilitates the BBB transit. We believe that this construct can be applicable to almost any protein or peptide for delivery to the CNS. To date, we have not seen a molecular or physical size restriction to the transport of proteins by this method.

Although the description given here is focused on the delivery of NEP, the application of this invention is not limited to this specific Aβ degrading enzyme. Other Aβ degrading enzymes which may prove successful in the same CNS delivery method include: insulin degrading enzyme (IDE), endothelin convertase enzyme (ECE), and/or a Serine Endo-Peptidase (SEP, a metalo-endopeptidase).

Additional embodiments comprise any protein, e.g., enzyme, that can degrade, e.g., clear, aggregrated proteins such as tau, syn Aβ include proteins involved in intracellular clearance of accumulated proteins.

We have recently shown that overexpression of Beclin1, the major autophagy regulating protein, can clear cells of the accumulated Aβ, thus showing that alteration in the autophagy pathway may be a valid approach for the clearance of accumulated Aβ. In alternative embodiments, other proteins that also can be used to practice this invention and be effective in regulating the autophagy pathway (and clear cells of accumulated Aβ) include: ATG7 autophagy related 7 homolog (Atg7), Beclin (e.g., Beclin 1 protein (coiled-coil, myosin-like BCL2 interacting protein), and/or ubiquitin carboxyl-terminal esterase L1 (ubiquitin thiolesterase) (UCHL1).

Additionally, other proteins may also be used to practice this invention and be effective at the clearing of accumulated Aβ include: proteins of the heat shock pathway (e.g., Heat shock proteins, or HSPs), proteins of the ubiquitin/proteosomal pathway (e.g., a ubiquitin), and proteins that regulate the production of APP.

The compositions and methods of this invention can deliver these and other proteins across the BBB for access to the whole CNS.

While the invention is not limited by any particular mechanism of action, FIG. 1 illustrates a diagrammatic representation of an exemplary concept of the invention.

A secreted NEP (secNEP) protein was generated by cloning the human NEP extracellular domain into the lentivirus plasmid, pBob. The secretory signal of pre-pro trypsin was cloned at the 5' end followed by the LDL-R binding domain of apolipoprotein B. The resulting construct was designated pLV-ApoBSecNep. A control construct was generated that contained the secreted NEP without the ApoB LDL-R binding domain (pLV-SecNep). As a control for transported proteins, a virus was generated as described above with eGFP, pre-pro trypsin secretory signal and the ApoB LDL-R binding domain (pLV-GFPApoB).

The amino acid sequence for ApoBSecNep is:

(SEQ ID NO: 1)
M S A L L I L A L V G A A V A D Y K D D D K T G
S S V I D A L Q Y K L E G T T R L T R K R G L K L
A T A L S L S N K F V E G S T G Y D D G I C K S S
D C I K S A A R L I Q N M D A T T E P C R D F F K
Y A C G G W L K R N V I P E T S S R Y G N F D I L
R D E L E V V L K D V L Q E P K T E D I V A V Q K
A K A L Y R S C I N E S A I D S R G G E P L L K L
L P D I Y G W P V A T E N W E Q K Y G A S W T A E
K A I A Q L N S K Y G K K V L I N L F V G T D D K
N S V N H V I H I D Q P R L G L P S R D Y Y E C T
G I Y K E A C T A Y V D F M I S V A R L I R Q E E
R L P I D E N Q L A L E M N K V M E L E K E I A N
A T A K P E D R N D P M L L Y N K M R L A Q I Q N
N F S L E I N G K P F S W L N F T N E I M S T V N
I S I T N E E D V V V Y A P E Y L T K L K P I L T
K S A R D L Q N L M S W R F I M D L V S S L S R T
Y K E S R N A F R K A L Y G T T S E T A T W R R C
A N Y V N G N M E N A V G R L Y V E A A F A G E S
K H V V E D L I A Q I R E V F I Q T L D D L T W M
D A E T K K R A E E K A L A I K E R I G Y P D D I
V S N D N K L N N E Y L E L N Y K E D E Y F E N I
I Q N L K F S Q S K Q L K K L R E K V D K D E W I
S G A A V V N A F Y S S G R N Q I V F P A G I L Q
P P F F S A Q Q S N S L N Y G G I G M V I G H E I
T H G F D D N G R N F N K D G D L V D W W T Q Q S
A S N F K E Q S Q C M V Y Q Y G N F S W D L A G G
Q H L N G I N T L G E N I A D N G G L G Q A Y R A
Y Q N Y I K K N G E E K L L P G L D L N H K Q L F
F L N F A Q V W C G T Y R P E Y A V N S I K T D V
H S P G N F R I I G T L Q N S A E F S E A F H C R
K N S Y M N P E K K C R V W

The amino acid sequence for human neprilysin is (see e.g., Miners (2009) J. Neuropathol. Exp. Neurol. 68(8), 902-914; or NCBI Reference Sequence: NP_009220.2):

(SEQ ID NO: 2)
  1 mgksesqmdi tdintpkpkk kqrwtpleis lsvlvlllti iavtmialya tyddgickss
 61 dciksaarli qnmdattepc tdffkyacgg wlkrnvipet ssrygnfdil rdelevvlkd
121 vlqepktedi vavqkakaly rscinesaid srggepllkl lpdiygwpva tenweqkyga -continued

```
181 swtaekaiaq lnskygkkvl inlfvgtddk nsvnhvihid qprlglpsrd yyectgiyke 241 actayvdfmi svarlirqee rlpidenqla lemnkvmele keianatakp edrndpmlly 301 nkmtlaqiqn nfsleingkp fswlnftnei mstvnisitn eedvvvyape yltklkpilt 361 kysardlqnl mswrfimdlv sslsrtykes rnafrkalyg ttsetatwrr canyvngnme 421 navgrlyvea afageskhvv edliaqirev fiqtlddltw mdaetkkrae ekalaikeri 481 gypddivsnd nklnneylel nykedeyfen iiqnlkfsqs kqlkklrekv dkdewisgaa 541 vvnafyssgr nqivfpagil qppffsaqqs nslnyggigm vigheithgf ddngrnfnkd 601 gdlvdwwtqq sasnfkeqsq cmvyqygnfs wdlaggqhln gintlgenia dngglgqayr 661 ayqnyikkng eekllpgldl nhkqlfflnf aqvwcgtyrp eyavnsiktd vhspgnfrii 721 gtlqnsaefs eafhcrknsy mnpekkcrvw
```

To determine if the newly generated secNEP was secreted and active, LV was produced and used to infect 293T cells. Cells culture supernate and lysates was collected 72 hours after virus infection and analyzed by Western blot. The NEP antibody recognized a band at ~100 kDa in the lysates of the 293T cells infected with the LV-NEP, LV-SecNEP and the LV-ApoBSecNEP (FIG. 2B). This band was not observed in uninfected 293T cells or cells infected with the LV-ApoBGFP virus indicating that neprilysin is not endogenously produced by the 293T cells.

Cell culture supernate was analyzed by Western blot to determine if the protein was secreted. Cells infected with the LV-SecNEP and LV-ApoBSecNEP contained the expected neprilysin reacting band at 100 kDa whereas control cells or cells infected with the LV-NEP did not (FIG. 2B).

Figure 3:
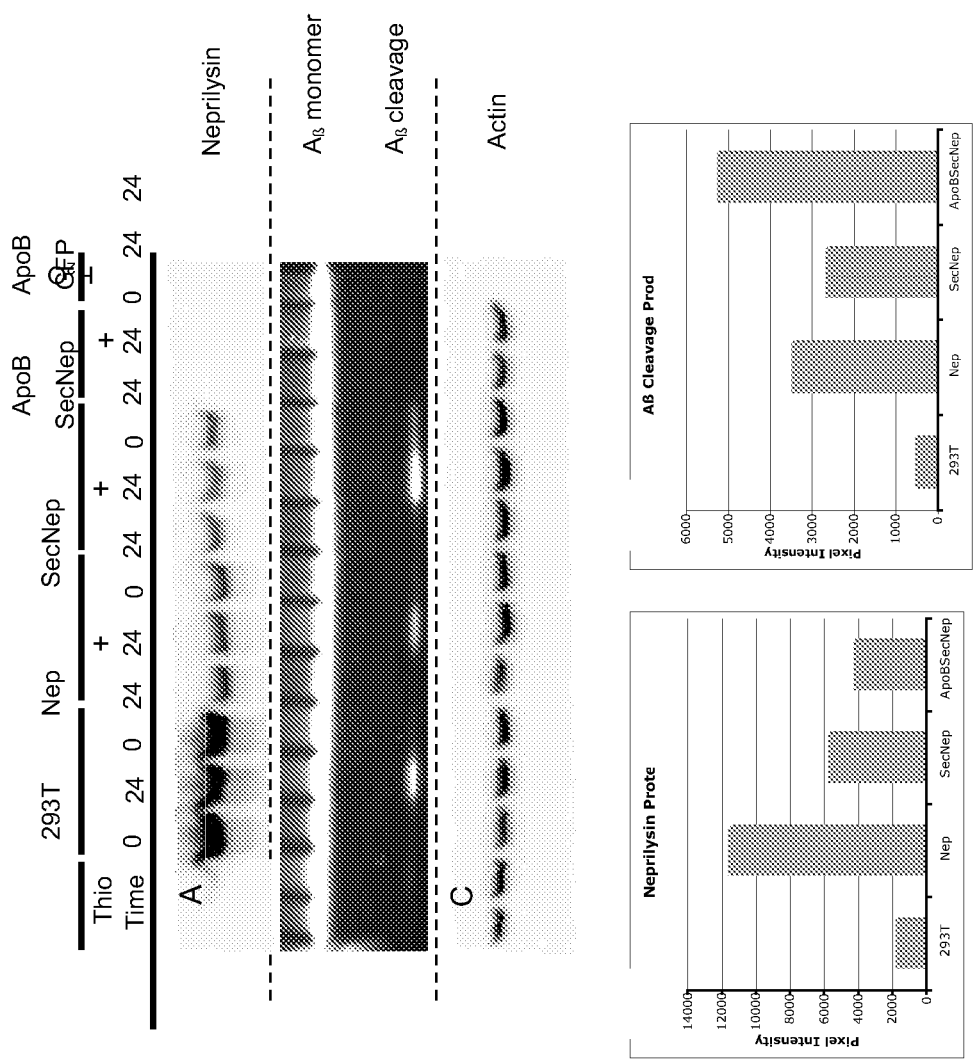
FIG. 3 illustrates data demonstrating that neprilysin protein expressed from the exemplary lentivirus expression construct of the invention in 293T cells is active in cleaving Aβ monomers: 293T cells were infected with the different lentiviruses (for 72 hours and whole cell lysate was collected.

In order to determine if the vector produced neprilysin protein constructs were enzymatically active, we incubated cell lysates or supernatant samples with a N-terminus FITC labeled Aβ (42) for 24 hours. Lysates of infected 293T cells showed increased neprilysin activity from all the NEP vectors tested with the normal neprilysin having a 6 fold increase in Aβ cleavage compared to uninfected 293T cells (FIG. 3). Of particular note, the SecNep and ApoB-SecNep proteins were present at reduced levels in the lysates of the infected cells, however the NEP activity was as efficient as wild type NEP (SecNep) or even 50% more (ApoB-SecNep).

Figure 4:
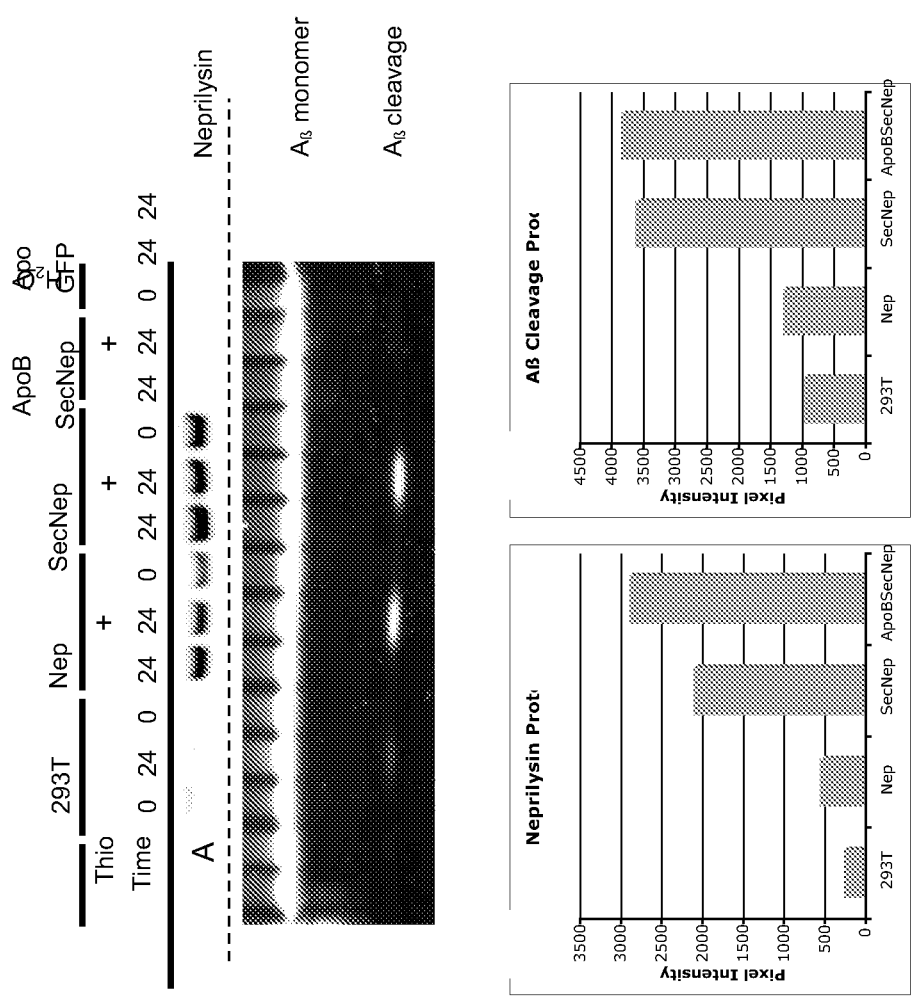
FIG. 4 illustrates data demonstrating that neprilysin secreted from cells infected with and expressing the exemplary lentivirus construct of the invention is active in cleaving Aβ monomers: 293T cells were infected with the different lentiviruses for 72 hours and supernate was collected and filtered; the upper panel of FIG. 4 (the Western blot gel radiograph) illustrates that neprilysin protein detection by Western blot (A), and the lower two panels of FIG. 4 graphically illustrate analysis of activity against a N-terminal FITC tagged Aβ protein; the left panel (graph) illustrates quantifying (by pixel intensity) of total neprilysin, and the right panel (graph) illustrates quantifying of the Aβ N-terminal cleavage product to analyze neprilysin activity, as discussed in Example 1, below.

To test the activity of the secNEP, the supernate from uninfected 293T cells or cells infected with any of the three NEP vectors was filtered with a 0.22 μm filter to remove any contaminating cells and then was subjected to the same N-terminus FITC labeled Aβ cleavage assay (FIG. 4). Little to no NEP product was observed from uninfected or LV-NEP infected cell supernate, however, as expected, NEP was present in the supernate of cells infected with either the LV-SecNEP or the LV-ApoBSecNEP vectors. The Aβ cleavage was detected at levels comparable to cell lysates activity only in those samples that had the secreted NEP. The Aβ cleavage was specific to the presence of NEP as the addition of thiorphan, a NEP specific blocker, reduced the formation of the Aβ cleavage product (data not shown).

In order to determine whether these vectors might be effective at reducing the levels of Aβ in vivo, we delivered $1\times10^9$ tdu of LV vector to APP tg mice via a single intra-peritoneal injection. Three months after injection, mice were sacrificed and brains were removed for analysis of Aβ and NEP.

Figure 5:
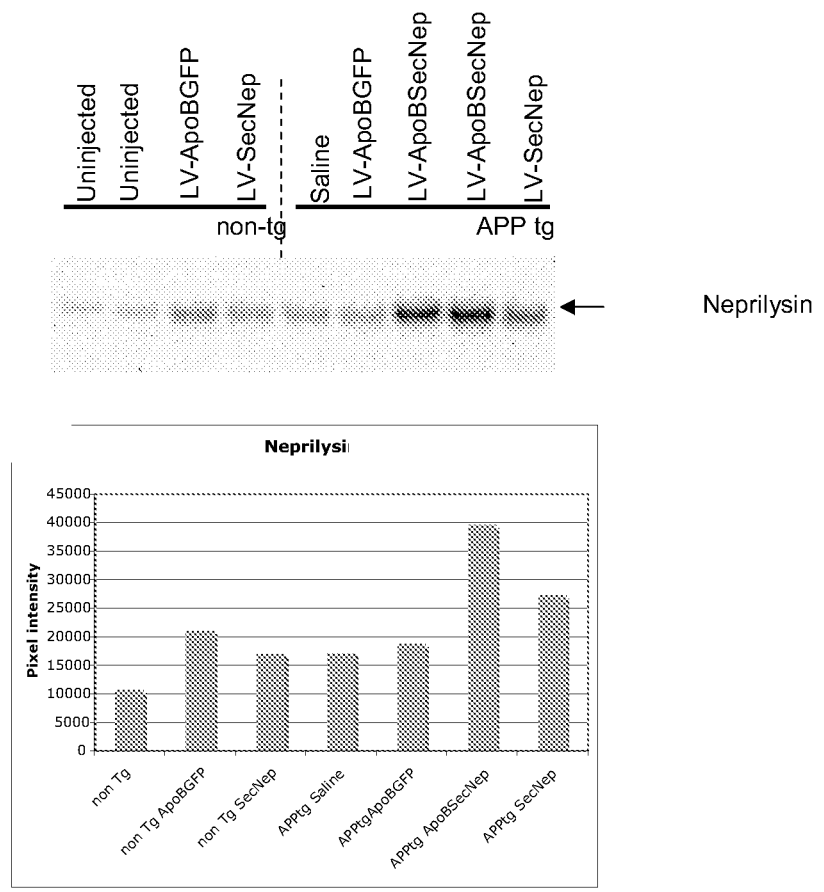
FIG. 5 illustrates data demonstrating that neprilysin is detected in the brains of mice that received the exemplary construct of the invention, the exemplary expression construct of this invention, the recombinant LV-ApoBSecNep virus, by intraperitoneal (IP, or i.p.) injection. APPtg (APP transgenic) and non tg (non-transgenic) mice received a single i.p. injection of the exemplary lentivirus constructs of the invention expressing either SecNep, ApoBSecNep or ApoBGFP. Three (3) months after injection, mice were sacrificed and total brain protein was analyzed by Western blot for neprilysin, as illustrated in the upper Western blot gel panel, or bands were quantified by densitometry (by pixel intensity), as graphically illustrated in the lower panel, as discussed in Example 1, below.
Figure 6:
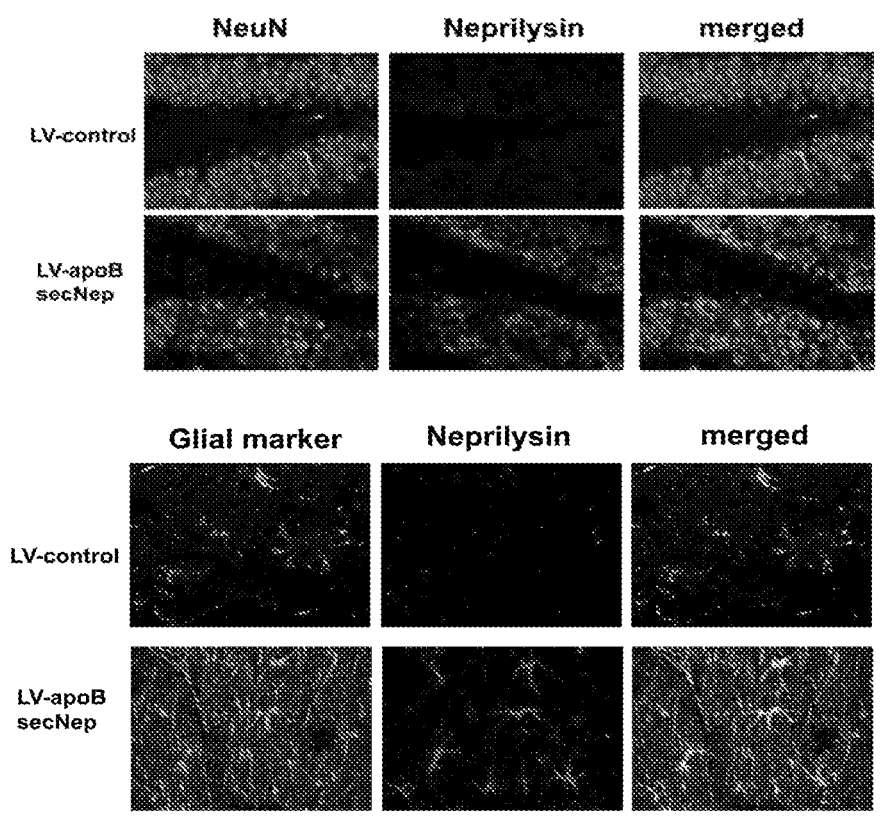
FIG. 6 illustrates micrographs showing that the exemplary chimeric ApoBSecNep protein of the invention is found in association with neurons and astrocytes following an i.p. injection of the exemplary lentivirus construct of the invention expressing the exemplary chimeric ApoBSecNep protein. APP tg mice received a single i.p. injection of the exemplary lentivirus expressing the exemplary chimeric ApoBSecNep protein of the invention or a control. Three (3) months after injection, mice were sacrificed and the brain was section and stained for neprilysin (red) and NeuN (neuron-specific nuclear protein) (A, green) or GFAP (or Glial Fibrillary Acidic Protein, the "glial marker") (green, B), as discussed in Example 1, below.

Whole brain analysis by Western blot for the NEP protein showed a 2 fold increase in the brains of mice that had received the LV-ApoBSecNep virus compared to uninjected or control injected mice (FIG. 5A) Immunocytochemical analysis of the brains of mice that had received either the LV-ApoBSecNEP or LV-control virus showed NEP specifically in the brains of mice that had received the ApoBSecNEP. Neprilysin protein co-localized with the neuronal marker, NeuN, in the dentate gyrus and the CA1 region of the hippocampus (FIG. 6A). In addition, there was considerable co-labeling of astrocytes (GFAP) and the NEP protein indicating that glia cells were also taking up the recombinant protein (FIG. 6B).

Figure 7:
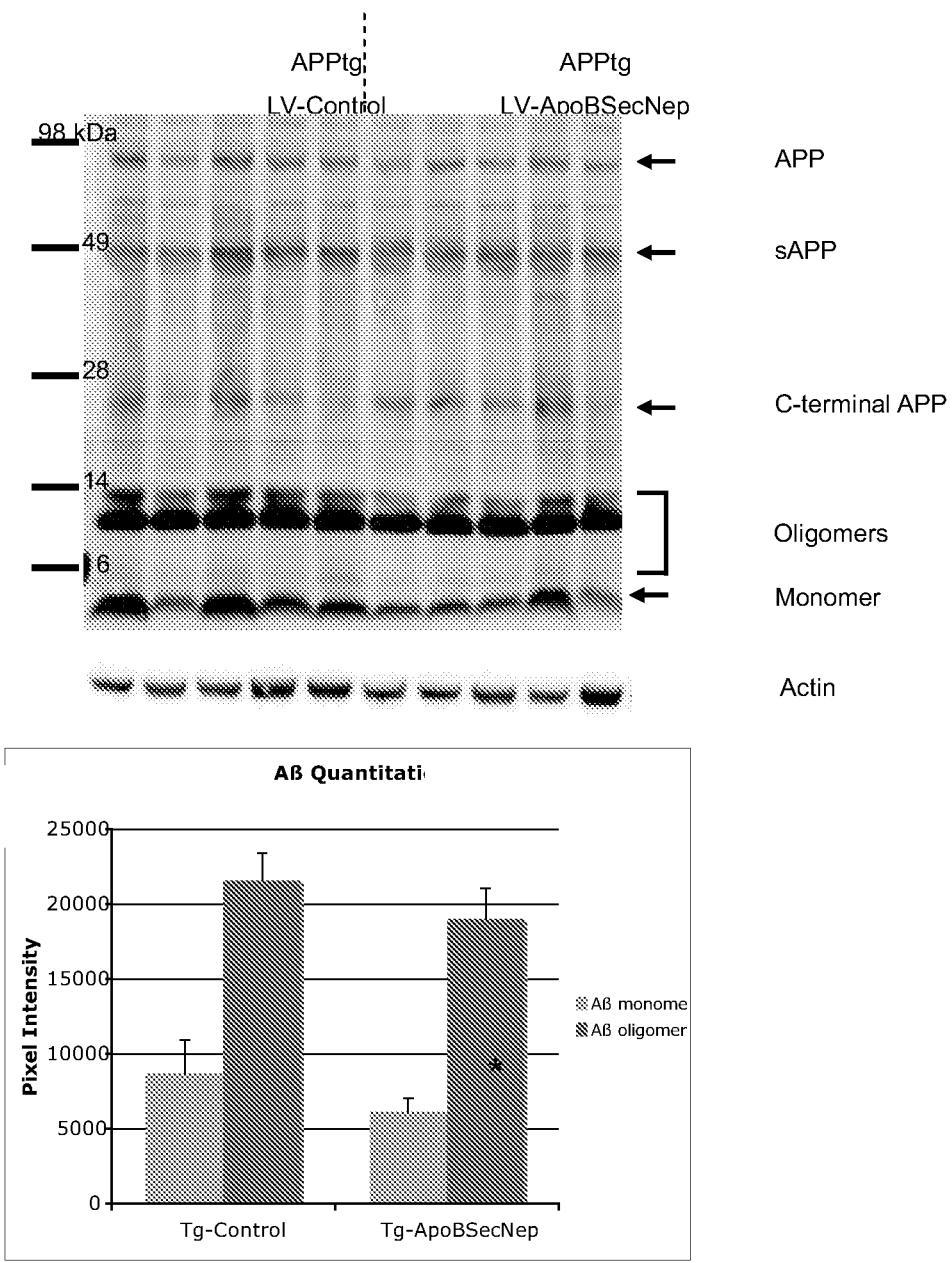
FIG. 7 illustrates data showing that Aβ monomer is reduced in mice following a single i.p. injection of the exemplary lentivirus construct of the invention expressing the exemplary chimeric ApoBSecNep protein of the invention. APP tg mice were injected i.p. with either LV-ApoBSecNep or LV-control. Three (3) months after injection, total protein from the brain was analyzed by Western blot for APP and Aβ (A)—radiograph of Western blot is upper panel; to ensure even loading actin was analyzed on the same blots (middle radiograph panel); and as illustrated by the lower panel graph, Aβ monomer and oligomer bands were quantified (by pixel intensity) by densitometry (B); *-p<0.05 compared to tg control mice, as discussed in Example 1, below.

Quantitation of APP and its cleavage products in the brains of APP tg mice that received either the LV-ApoBSecNEP or LV-control, showed a significant reduction in Aβ monomer when mice were treated with the LV-ApoBSecNep (FIG. 7). Similarly, there was a slight reduction in the Aβ oligomers in these same mice. In contrast, there was no difference in APP or secreted APP (sAPP).

Figure 8:
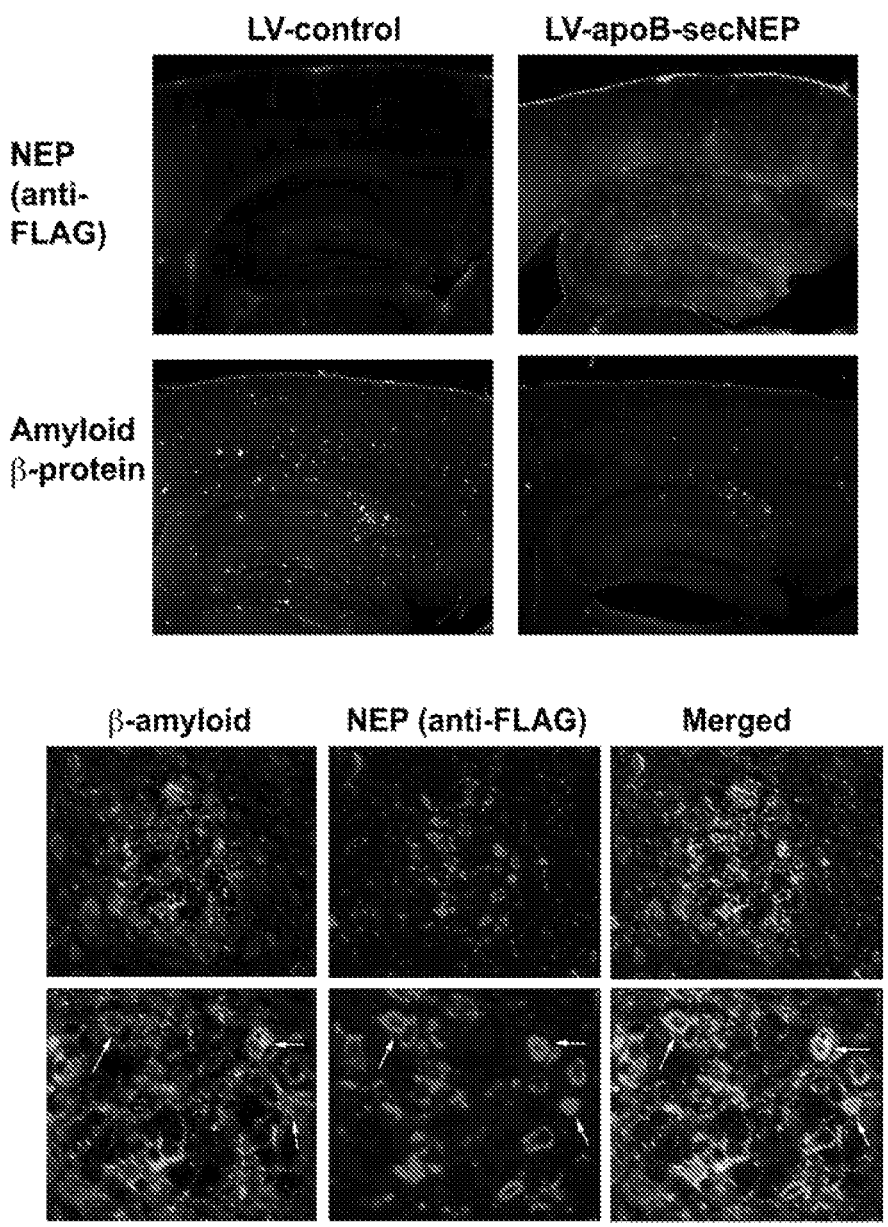
FIG. 8 illustrates micrographs showing that the exemplary chimeric ApoBSecNep protein of the invention is associated with reduced plaques and with intracellular Aβ in vivo. APPtg mice received an i.p. injection of either the exemplary chimeric LV-ApoBSecNep or LV-control and 3 months later the brain was sectioned and stained for the exemplary chimeric ApoBSecNep by the FLAG epitope tag (red) and for Aβ (green); upper panels illustrate low power photos of the whole brain; and the lower panels illustrate higher power images of individual cells indicating co-localization of neprilysin (with intracellular Aβ), as discussed in Example 1, below.

In agreement with the western blot data, immunocytochemical analysis of these mice revealed a reduction in Aβ accumulation in the neocortex and hippocampus (FIG. 8A). In particular there was a reduction in visible plaques in the cortex and the hippocampus. Co-labeling for the recombinant NEP protein and Aβ in the CNS showed considerable co-staining of the two proteins indicating that the recombinant ApoBSecNEP is being taken up by cells that are loaded with the Aβ protein (FIG. 8B).

To summarize, the LV vectors expressing SecNEP and ApoBSecNEP express the NEP protein and secrete the protein into the supernate of infected cells. In addition, these NEP constructs are active at cleaving the Aβ 1-42 protein in a similar manner to the wildtype NEP. The hybrid ApoBSecNEP produced from the LV in mice crosses the BBB and in APP tg reduces the levels of AD-like neuropathology including Aβ accumulation and neurodegeneration. The hybrid ApoBSecNEP was identified in neurons and glial cells and we demonstrated that it retained it high activity.

Studies in APP tg mice can be used for: 1) further behavioral analysis; 2) testing of variant potentially more efficient constructs with AAV and LV and regulatable promoters; 3) peripheral injections of the recombinant ApoBSecNEP; 4) novel hybrid peptides expressing other Aβ degrading enzymes (IDE), lysosomal proteins (cathepsin D), autophagy molecules (Beclin) and proteosomal components (UCHL-1).

The amino acid and nucleic acid sequences used to make the constructs and hybrid/chimeric proteins of this invention are well known in the art, e.g., as noted for human neprilysin, above. For example, other exemplary sequences that can be used in full or in part to construct a hybrid/chimeric protein of this invention includes, e.g.:

The amino acid sequence for human beclin 1 is (see e.g., Zalckvar (2009) Autophagy 5 (5), 720-722 (2009); or NCBI Reference Sequence: NP_003757.1):

(SEQ ID NO: 3)
```
  1 megsktsnns tmqvsfvcqr csqplkldts fkildrvtiq eltaplltta qakpgetqee
 61 etnsgeepfi etprqdgvsr rfipparmms tesansftli geasdggtme nlsrrlkvtg
121 dlfdimsgqt dvdhplceec tdtlldqldt qlnvtenecq nykrcleile qmneddseql
181 qmelkelale eerliqeled veknrkivae nlekvqaeae rldqeeaqyq reysefkrqq
241 lelddelksv enqmryaqtq ldklkktnvf natfhiwhsg qfgtinnfrl grlpsvpvew
301 neinaawgqt vlllhalank mglkfqryrl vpygnhsyle sltdkskelp lycsgglrff
361 wdnkfdhamv afldcvqqfk eevekgetrf clpyrmdvek gkiedtggsg gsysiktqfn
421 seeqwtkalk fmltnlkwgl awvssqfynk
```

The amino acid sequence for human insulin degrading enzyme (IDE) is: (see also e.g., NCBI Reference Sequence: NM_004969.4

(SEQ ID NO: 4)
```
MRYRLAWLLHPALPSTFRSVLGARLPPPERLCGFQKKTYSKMNNPAIKR
IGNHITKSPEDKREYRGLELANGIKVLLISDPTTDKSSAALDVHIGSLS
DPPNIAGLSHFCEHMLFLGTKKYPKENEYSQFLSEHAGSSNAFTSGEHT
NYYFDVSHEHLEGALDRFAQFFLCPLFDESCKDREVNAVDSEHEKNVMN
DAWRLFQLEKATGNPKHPFSKFGTGNKYTLETRPNQEGIDVRQELLKFH
SAYYSSNLMAVCVLGRESLDDLTNLVVKLFSEVENKNVPLPEFPEHPFQ
EEHLKQLYKIVPIKDIRNLYVTFPIPDLQKYYKSNPGHYLGHLIGHEGP
GSLLSELKSKGWVNTLVGGQKEGARGFMFFIINVDLTEEGLLHVEDIIL
HMFQYIQKLRAEGPQEWVFQECKDLNAVAFRFKDKERPRGYTSKIAGIL
HYYPLEEVLTAEYLLEEFRPDLIEMVLDKLRPENVRVAIVSKSFEGKTD
RTEEWYGTQYKQEAIPDEVIKKWQNADLNGKFKLPTKNEFIPTNFEILP
LEKEATPYPALIKDTAMSKLWFKQDDKFFLPKACLNFEFFSPFAYVDPL
HCNMAYLYLELLKDSLNEYAYAAELAGLSYDLQNTIYGMYLSVKGYNDK
QPILLKKIIEKMATFEIDEKRFEIIKEAYMRSLNNFRAEQPHQHAMYYL
RLLMTEVAWTKDELKEALDDVTLPRLKAFIPQLLSRLHIEALLHGNITK
QAALGIMQMVEDTLIEHAHTKPLLPSQLVRYREVQLPDRGWFVYQQRNE
VHNNCGIEIYYQTDMQSTSENMFLELFCQIISEPCFNTLRTKEQLGYIV
FSGPRRANGIQGLRFIIQSEKPPHYLESRVEAFLITMEKSIEDMTEEAF
QKHIQALAIRRLDKPKKLSAECAKYWGEIISQQYNFDRDNTEVAYLKTL
TKEDIIKFYKEMLAVDAPRRHKVSVHVLAREMDSCPVVGEFPCQNDINL
SQAPALPQPEVIQNMTEFKRGLPLFPLVKPHINFMAAKL
```

The amino acid sequence for human autophagy-related cysteine endopeptidase 2 isoform A is: (see also e.g., NCBI Reference Sequence: NP_443168.2):

(SEQ ID NO: 5)
```
  1 mesvlskyed qitiftdyle eypdtdelvw ilgkqhllkt ekskllsdis arlwftyrrk
 61 fspiggtgps sdagwgcmlr cgqmmlaqal icrhlgrdws wekqkeqpke yqrilqcfld
121 rkdccysihq maqmgvgegk sigewfgpnt vaqvlkklal fdewnslavy vsmdntvvie
181 dikkmcrvlp lsadtagdrp pdsltasnqs kgtsaycsaw kplllivplr lginqinpvy
241 vdafkecfkm pqslgalggk pnnayyfigf lgdelifldp httqtfvdte engtvndqtf
301 hclqspqrmn ilnldpsval gffckeekdf dnwcslvqke ilkenlrmfe lvqkhpshwp
361 pfvppakpev tttgaefids teqleefdle edfeilsv
```

The amino acid sequence for human autophagy-related cysteine endopeptidase 2 isoform B is: (see also e.g., NCBI Reference Sequence: NP_840054.1):

(SEQ ID NO: 6)
```
  1 mesvlskyed qitiftdyle eypdtdelvw ilgkqhllkt ekskllsdis arlwftyrrk
 61 fspiggtgps sdagwgcmlr cgqmmlaqal icrhlgrdws wekqkeqpke yqrilqcfld
121 rkdccysihq maqmgvgegk sigewfgpnt vaqvlkklal fdewnslavy vsmdntvvie
181 dikkmcrvlp lsadtagdrp pdsltasnqs delifldpht tqtfvdteen gtvndqtfhc
241 lqspqrmnil nldpsvalgf fckeekdfdn wcslvqkeil kenlrmfelv qkhpshwppf
301 vppakpevtt tgaefidste qleefdleed feilsv
```

The amino acid sequence for the C54 family autophagy-related protein APG4 autophagy 4 homolog C isoform 8 is: (see also e.g., NCBI Reference Sequence: NP_835739.1):

(SEQ ID NO: 7)
```
  1 meatgtdevd klktkfisaw nnmkyswvlk tktyfsrnsp vlllgkcyhf kyededktlp
 61 aesgctiedh viagnveefr kdfisriwlt yreefpqieg salttdcgwg ctlrtgqmll
121 aqglilhflg rawtwpdaln iensdseswt shtvkkftas feaslsgere fktptislke
181 tigkysddhe mrnevyhrki iswfgdspla lfglhqliey gkksgkkagd wygpavvahi
241 lrkaveearh pdlqgitiyv aqdctvynsd vidkqsasmt sdnaddkavi ilvpvrlgge
301 rtntdylefv kgilsleycv giiggkpkqs yyfagfqdds liymdphycq sfvdvsikdf
361 pletfhcpsp kkmsfrkmdp sctigfycrn vqdfkrasee itkmlkfssk ekyplftfvn
421 ghsrdydfts tttneedlfs edekkqlkrf steefvll
```

The amino acid sequence for human cysteine protease ATG4D (or autophagy-related protein 4 homolog D) is: (see also e.g., Swiss-Prot: Q86TL0.1):

(SEQ ID NO: 8)
```
  1 mnsyspaaaq yrssspedar rrpearrprg prgpdpnglg psgasgpalg spgagpsepd
 61 evdkfkakfl tawnnvkygw vvksrtsfsk issihlcgrr yrfegegdiq rfqrdfvsrl
121 wltyrrdfpp lpggcltsdc gwgcmlrsgq mmlaqglllh flprdwtwae gmglgppels
181 gsaspsryhg parwmpprwa qgapeleqer rhrqivswfa dhprapfglh rlvelgqssg
241 kkagdwygps lvahilrkav escsdvtrlv vyvsqdctvy kadvarlvar pdptaewksv
301 vilvpvrlgg etlnpvyvpc vkellrcelc lgimggkprh slyfigyqdd fllyldphyc
361 qptvdvsqad fplesfhcts prkmafakmd psctvgfyag drkefetlcs eltrvlssss
421 aterypmftl aeghaqdhsl ddlcsqlaqp tlrlprtgrl lrakrpssed fvfl
```

The amino acid sequence for human ubiquitin is: (see also e.g., GenBank: CAA44911.1):

(SEQ ID NO: 9)
```
  1 mqifvktltg ktitleveps dtienvkaki qdkegippdq qrlifagkql edgrtlsdyn
 61 iqkestlhlv lrlrggakkr kkksyttpkk nkhkrkkvkl avlkyykvde ngkisrlrre
121 cpsdecgagv fmashfdrhy cgkccltycf nkpedk
```

The amino acid sequence for human transtherytin (TTR) protein is: (see also e.g., NCBI Reference Sequence: NM_000371.3):

(SEQ ID NO: 10)
MASHRLLLLCLAGLVFVSEAGPTGTGESKCPLMVKVLDAVRGSPAINVA
VHVFRKAADDTWEPFASGKTSESGELHGLTTEEEFVEGIYKVEIDTKSY
WKALGISPFHEHAEVVFTANDSGPRRYTIAALLSPYSYSTTAVVTNPKE

The amino acid sequence for human Rac1 (Ras-related C3 botulinum toxin substrate 1) protein is: (see also e.g., NCBI Reference Sequence: NM_018890.3):

(SEQ ID NO: 11)
MQAIKCVVVGDGAVGKTCLLISYTTNAFPGEYIPTVFDNYSANVMVDGK
PVNLGLWDTAGQEDYDRLRPLSYPQTVGETYGKDITSRGKDKPIADVFL
ICFSLVSPASFENVRAKWYPEVRHHCPNTPIILVGTKLDLRDDKDTIEK

-continued
LKEKKLTPITYPQGLAMAKEIGAVKYLECSALTQRGLKTVFDEAIRAVL
CPPPVKKRKRKCLLL

REFERENCES

1. Spencer, B. J. and I. M. Verma, Targeted delivery of proteins across the blood-brain barrier. Proc Natl Acad Sci USA, 2007.
2. Carter, T. L., et al., Brain neprilysin activity and susceptibility to transgene-induced Alzheimer amyloidosis. Neurosci Lett, 2006. 392(3): p. 235-9.
3. El-Amouri, S. S., et al., Neprilysin: an enzyme candidate to slow the progression of Alzheimer's disease. Am J Pathol, 2008. 172(5): p. 1342-54.
4. Farris, W., et al., Loss of neprilysin function promotes amyloid plaque formation and causes cerebral amyloid angiopathy. Am J Pathol, 2007. 171(1): p. 241-51.

5. Fossiez, F., et al., Secretion of a functional soluble form of neutral endopeptidase-24.11 from a baculovirus-infected insect cell line. Biochem J, 1992. 284 (Pt 1): p. 53-9.
6. Fukami, S., et al., Abeta-degrading endopeptidase, neprilysin, in mouse brain: synaptic and axonal localization inversely correlating with Abeta pathology. Neurosci Res, 2002. 43(1): p. 39-56.
7. Hama, E., et al., Clearance of extracellular and cell-associated amyloid beta peptide through viral expression of neprilysin in primary neurons. J Biochem, 2001. 130(6): p. 721-6.
8. Hemming, M. L., et al., Reducing amyloid plaque burden via ex vivo gene delivery of an Abeta-degrading protease: a novel therapeutic approach to Alzheimer disease. PLoS Med, 2007. 4(8): p. e262.
9. Hemming, M. L., D. J. Selkoe, and W. Farris, Effects of prolonged angiotensin-converting enzyme inhibitor treatment on amyloid beta-protein metabolism in mouse models of Alzheimer disease. Neurobiol Dis, 2007. 26(1): p. 273-81.
10. Hong, C. S., et al., Herpes simplex virus RNAi and neprilysin gene transfer vectors reduce accumulation of Alzheimer's disease-related amyloid-beta peptide in vivo. Gene Ther, 2006. 13(14): p. 1068-79.
11. Huang, S. M., et al., Neprilysin-sensitive synapse-associated amyloid-beta peptide oligomers impair neuronal plasticity and cognitive function. J Biol Chem, 2006. 281(26): p. 17941-51.
12. Iijima-Ando, K., et al., Overexpression of neprilysin reduces Alzheimer's amyloid-beta 42 (Abeta 42)-induced neuron loss and intraneuronal Abeta 42 deposits, but causes a reduction in CREB-mediated transcription, age-dependent axon pathology and premature death in Drosophila. J Biol Chem, 2008.
13. Leissring, M. A., et al., Enhanced proteolysis of beta-amyloid in APP transgenic mice prevents plaque formation, secondary pathology, and premature death. Neuron, 2003. 40(6): p. 1087-93.
14. Marr, R. A., et al., Neprilysin gene transfer reduces human amyloid pathology in transgenic mice. J Neurosci, 2003. 23(6): p. 1992-6.
15. Mohajeri, M. H., et al., Anti-amyloid activity of neprilysin in plaque-bearing mouse models of Alzheimer's disease. FEBS Lett, 2004. 562(1-3): p. 16-21.
16. Poirier, R., et al., Neuronal neprilysin overexpression is associated with attenuation of Abeta-related spatial memory deficit. Neurobiol Dis, 2006. 24(3): p. 475-83.
17. Bickel, U., T. Yoshikawa, and W. M. Pardridge, Delivery of peptides and proteins through the blood-brain barrier. Adv Drug Deliv Rev, 2001. 46(1-3): p. 247-79.
18. Poduslo, J. F., G. L. Curran, and C. T. Berg, Macromolecular permeability across the blood-nerve and blood-brain barriers. Proc Natl Acad Sci USA, 1994. 91(12): p. 5705-9.
19. Iwata, N., M. Higuchi, and T. C. Saido, Metabolism of amyloid-beta peptide and Alzheimer's disease. Pharmacol Ther, 2005. 108(2): p. 129-48.
20. Pardridge, W. M., Molecular biology of the blood-brain barrier. Mol Biotechnol, 2005. 30(1): p. 57-70.
21. Blomer, U., A. Ganser, and M. Schen, Invasive drug delivery. Adv Exp Med Biol, 2002. 513: p. 431-51.
22. Suhr, S. T. and F. H. Gage, Gene therapy in the central nervous system: the use of recombinant retroviruses. Arch Neurol, 1999. 56(3): p. 287-92.
23. Schlageter, K. E., et al., Microvessel organization and structure in experimental brain tumors: microvessel populations with distinctive structural and functional properties. Microvasc Res, 1999. 58(3): p. 312-28.
24. Rubin, L. L. and J. M. Staddon, The cell biology of the blood-brain barrier. Annu Rev Neurosci, 1999. 22: p. 11-28.
25. Stefansson, S., et al., Glycoprotein 330/low density lipoprotein receptor-related protein-2 mediates endocytosis of low density lipoproteins via interaction with apolipoprotein B100. J Biol Chem, 1995. 270(33): p. 19417-21.
26. Brown, M. S, and J. L. Goldstein, A receptor-mediated pathway for cholesterol homeostasis. Science, 1986. 232 (4746): p. 34-47.
27. Boren, J., et al., Identification of the low density lipoprotein receptor-binding site in apolipoprotein B100 and the modulation of its binding activity by the carboxyl terminus in familial defective apo-B100. J Clin Invest, 1998. 101(5): p. 1084-93.
28. Hussain, M. M., D. K. Strickland, and A. Bakillah, The mammalian low-density lipoprotein receptor family. Annu Rev Nutr, 1999. 19: p. 141-72.

Example 2

Administration of Compositions of the Invention Improve Memory and Learning Deficits in Individuals with Alzheimer's Disease (AD)

Using an art-recognized animal model for Alzheimer's Disease (AD), this example presents data demonstrating that administration of exemplary compositions of the invention can improve memory and learning deficits in individuals with Alzheimer's Disease (AD).

Experimental Procedure

In order to evaluate the functional effects of long term treatment with ApoB-sec-Nep groups of APP tg animals received IP injections with the following lentiviruses: a) empty control, b) secNep, c) ApoB-secNep, d) ApoB-GFP. A total of 4 animals per group (age 6 months) were included.

After 3 months of the injections, mice were tested in the water maze for behavioral performance. For this purpose, a pool (diameter 180 cm) was filled with opaque water (24° C.) and mice were first trained to locate a visible platform (days 1-3) and then a submerged hidden platform (days 4-7) in three daily trials 2-3 min apart. Mice that failed to find the hidden platform within 90 s were placed on it for 30 s. The same platform location was used for all sessions and all mice. The starting point at which each mouse was placed into the water was changed randomly between two alternative entry points located at a similar distance from the platform. On day 8, another visible platform trial was performed to exclude differences in motivation and fatigue. Time to reach the platform (latency), path length, and swim speed were recorded with a Noldus Instruments ETHOVISION™ video tracking system (San Diego Instruments, San Diego, Calif.) set to analyze two samples per second. All experiments described were approved by the animal subjects committee at the University of California at San Diego (UCSD) and were performed according to NIH recommendations for animal use. After the water maze mice were sacrificed and the brains removed for biochemical and neuropathological examination.

Results

This experiment showed that control non-tg mice treated with LV-control performed normally in the maze and after 3 days of learning in the visible platform. From days 4 to 7 the non-tg mice showed spatial learning recognition and memory curve intact.

In contrast APP tg mice treated with displayed poor performance in the invisible platform. Similarly APP tg mice treated with LV-GFP displayed impaired ability to find the invisible platform after the 3 days of training. The learning curves for days 4-7 were statistically different (one way ANOVA poshoc Dunnet, p<0.05) between the nontg and the APP tg treated with LV-control or LV-GFP.

In contrast, APP tg mice treated with LV-apoB-sec NEP, displayed an improved performance in terms of spatial learning and memory on days 4-7. The slope of the learning curve in the APP tg treated with LV-apoB-sec NEP was statistically different (one way ANOVA poshoc Dunnet, p<0.05) when compared to the APP tg treated with LV-control or LV-GFP. The APP tg mice treated with treated with LV-secNep showed a trend toward an improvement, however this was not statistically significant. After the completion of the behavioral analysis, mice were sacrificed and the brains removed. Neuropathological examination corroborated that in the mice that received LV-apoB-sec NEP, the hybrid protein was present in the brain and accumulated in the hippocampus. The levels of Abeta in the hippocampus were reduced in the mice that received LV-apoB-sec NEP compared to APP tg treated with LV-control or LV-GFP.

In conclusion, when expressed at sufficiently high levels from the periphery, the exemplary composition of the invention apoB-sec NEP is capable of crossing into the CNS and ameliorating the behavioral deficits in APP tg mouse models of AD. Thus, because this is an art-accepted model of AD, these data demonstrate that exemplary compositions of the invention are effective in ameliorating the deleterious behavioral and/or memory or learning effects of AD; and exemplary compositions of the invention are effective in reversing and improving the memory or learning deficits caused by AD.

Figure 9:
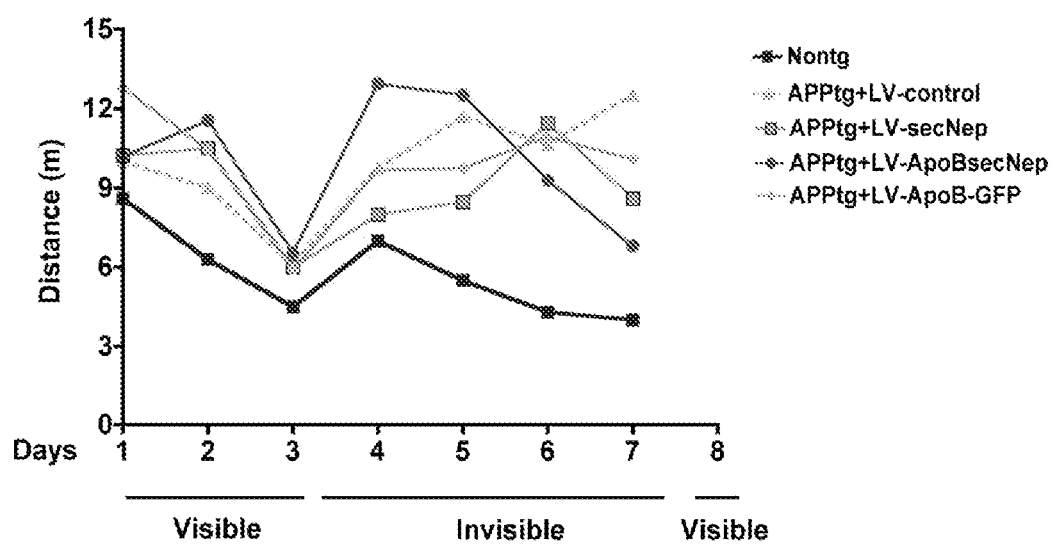
FIG. 9 graphically illustrates the behavioral effects of the exemplary composition of the invention LV-apoB-secNep in APP tg mice, as described in detail in Example 2, below.

FIG. 9 illustrates the behavioral effects of LV-apoB-sec-Nep in APP tg mice. Mice were tested in the water maze for 7 days. The first 3 days was training in the visible platform and days 4 to 7 was learning and memory testing in the invisible platform test. Non-tg mice (blue) performed normally as expected and display a learning curve from days 4-7. APP tg mice treated with control (light blue) or ApoB-GFP (orange) performed poorly. APP tg mice treated with LV-apoB-secNep (red) performed at comparable levels to the non-tg.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated, synthetic or recombinant chimeric polypeptide comprising a sequence as set forth in SEQ ID NO:1:
   (1) a low-density lipoprotein receptor (LDLR)-binding apolipoprotein B (apoB) peptide, and
   (2) a secreted neprilysin protein (secNEP), wherein the N-terminus of the secNEP is recombinantly fused or chemically joined to the carboxy terminus of the LDLR-binding apoB peptide.

2. A pharmaceutical composition or formulation comprising: the chimeric polypeptide of claim 1.

3. A liposome comprising the chimeric polypeptide of claim 1.

4. A nanoparticle comprising the chimeric polypeptide of claim 1.

5. A kit comprising: the chimeric polypeptide of claim 1.

6. The isolated, synthetic or recombinant chimeric polypeptide of claim 1, wherein the polypeptide further comprises a detection or a purification facilitating domain.

7. The isolated, synthetic or recombinant chimeric polypeptide of claim 1, further comprising an additional protein, wherein the additional protein is joined or fused to an amino terminal or a carboxy terminal end of the chimeric polypeptide.

8. The isolated, synthetic or recombinant chimeric polypeptide of claim 1, further comprising at least one pharmaceutically acceptable excipient.

9. The pharmaceutical composition or formulation of claim 2, formulated as an aqueous suspension, a solid, a liquid, a powder, an emulsion, a lyophilized powder, a spray, a cream, a lotion, a controlled release formulation, a tablet, a pill, a gel, a liposome, on a patch, in an implant, on a tape, a dragee, a capsule, a lozenge, a gel, a syrup, a slurry and/or a suspension.

10. A kit comprising at least one pharmaceutical composition or formulation of claim 2.

11. The kit of claim 5, further comprising instructions on how to use the chimeric polypeptide.

12. The kit of claim 10, further comprising instructions on how to use the pharmaceutical composition or formulation.

13. The isolated, synthetic or recombinant chimeric polypeptide of claim 1, further comprising a non-protein moiety.

14. An isolated, synthetic or recombinant chimeric polypeptide consisting of the chimeric polypeptide of claim 1.

15. A liposome comprising the pharmaceutical composition or formulation of claim 2.

16. A nanoparticle comprising the pharmaceutical composition or formulation of claim 2.

* * * * *